United States Patent
Satake et al.

(10) Patent No.: US 6,427,128 B1
(45) Date of Patent: Jul. 30, 2002

(54) APPARATUS AND METHOD FOR EVALUATING QUALITY OF GRANULAR OBJECT

(75) Inventors: Satoru Satake, Tokyo; Manabu Ikeda, Hiroshima; Satoru Takashita, Hiroshima; Takahiro Doi, Hiroshima, all of (JP)

(73) Assignee: Satake Corporation, Tokyo (JP)

( * ) Notice: Subject to any disclaimer, the term of this patent is extended or adjusted under 35 U.S.C. 154(b) by 0 days.

(21) Appl. No.: 09/556,947

(22) Filed: Apr. 21, 2000

(30) Foreign Application Priority Data

| Apr. 22, 1999 | (JP) | ............................................. 11-115405 |
| Jul. 16, 1999 | (JP) | ............................................. 11-203921 |
| Jul. 30, 1999 | (JP) | ............................................. 11-218091 |

(51) Int. Cl.[7] ............................................. G01N 37/00
(52) U.S. Cl. ........................... 702/81; 209/580; 209/587; 356/240.1; 356/376; 356/402
(58) Field of Search ............................. 702/29, 81, 82, 702/83, 84, 182, 183; 356/376, 402, 419, 432, 445, 446, 447; 250/223 R, 339.01, 339.07, 339.11, 339.12, 341.8, 358.1, 559.01, 910; 209/580, 587

(56) References Cited

U.S. PATENT DOCUMENTS

| 4,371,081 A | 2/1983 | Satake ......................... 209/580 |
| 4,429,225 A | 1/1984 | Fumoto et al. .............. 250/353 |
| 4,630,736 A | 12/1986 | Maughan et al. ........... 209/587 |
| 4,699,274 A | 10/1987 | Saika .......................... 209/587 |
| 4,742,228 A | 5/1988 | Bischoff .................... 250/341.1 |
| 4,801,804 A | 1/1989 | Rosenthal ................. 250/341.2 |
| 5,135,114 A | 8/1992 | Satake et al. .............. 209/558 |
| 5,220,400 A | 6/1993 | Anderson et al. ......... 356/240.1 |
| 5,254,858 A | 10/1993 | Wolfman et al. ....... 250/339.06 |
| 5,258,825 A | 11/1993 | Reed et al. ................. 356/402 |
| 5,443,164 A | 8/1995 | Walsh et al. ................ 209/580 |
| 5,638,961 A | 6/1997 | Satake et al. ............... 209/580 |
| 5,669,511 A | * 9/1997 | Satake et al. ............... 209/580 |
| 5,735,402 A | 4/1998 | Pezzoli et al. .............. 209/129 |
| 6,097,493 A | * 8/2000 | Satake et al. ............... 356/376 |

FOREIGN PATENT DOCUMENTS

| EP | 0443769 A2 | 8/1991 | ................. 209/539 |
| EP | 08015141 A | 1/1996 | |
| EP | 0727260 | 8/1996 | ................. 209/580 |
| EP | 0834731 A2 | 4/1998 | ................. 436/20 |

OTHER PUBLICATIONS

Nippon Shokuhin Kogyo Gakkaishi, "Applicability of Near Infrared Reflectance Method to Moisture, Protein and Ash Measurements of Buckwheat Flours", 1984, vol. 31, No. 3, pp. 200–202.

Nippon Shokuhin Kogyo Gakkaishi, "Near Infrared Reflectance Analysis for Determining Moisture, Protein and Ash Contents in Home–grown Wheat Flours", 1984, vol. 31, No. 1, pp. 50–53.

* cited by examiner

Primary Examiner—John S. Hilten
Assistant Examiner—John Le
(74) Attorney, Agent, or Firm—Fish & Richardson P.C.

(57) ABSTRACT

A quality evaluation method for granular objects includes the steps of: irradiating objects from a front side and a back side; taking a reflection light image and a transmission light image from both the front and back sides of the objects; obtaining optical information of the objects by image-processing the reflection and transmission light images; obtaining shape information of the objects based on the optical information; determining the quality of each of the objects based on the optical information and the shape information; and counting the numbers of objects per quality and obtaining ratios of the objects per quality against the total number of objects. The data from the front and the back sides of the granular object are analyzed to enhance the precision of the results of the quality analysis, and in particular, to enhance the precision in detecting cracks.

12 Claims, 22 Drawing Sheets

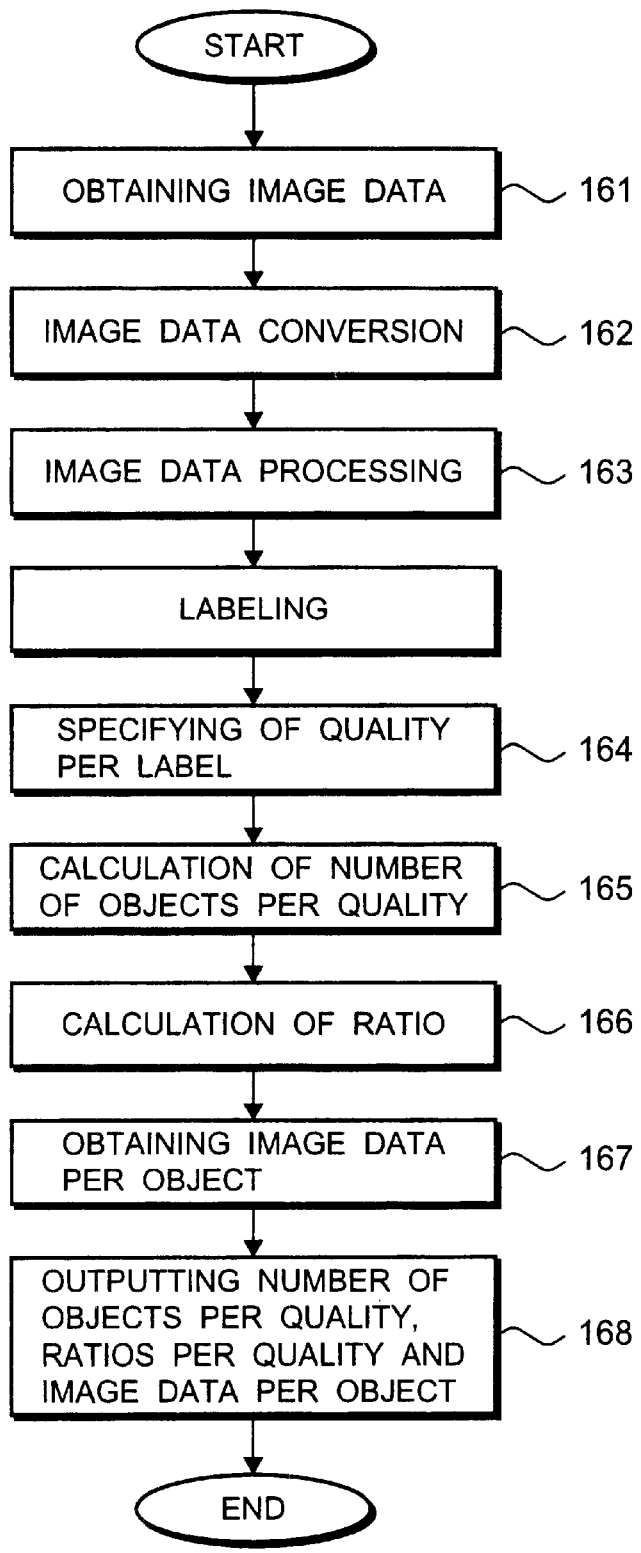

Fig. 18

RICE QUALITY MEASUREMENT ANALYSIS RESULTS

Production: Higashi hiroshima-shi,
District    Hiroshima- ken
Kind       : chuseishinsenbon Analysis Date: 1998.5.25
Harvest Date : 1998.10.3
Sample No.   : 0001658947

Quality Ranking: 2

| ITEM | NUMBER OF GRAINS (GRAINS) | NUMBER OF GRAIN RATIO (%) | WEIGHT RATIO (%) | ITEM | NUMBER OF GRAINS (GRAINS) | NUMBER OF GRAIN RATIO (%) | WEIGHT RATIO (%) |
|---|---|---|---|---|---|---|---|
| REGULAR GRAIN | 748 | 74.8 | 79.2 | REGULAR GRAIN | 748 | 74.8 | 79.2 |
| GREEN IMMATURE GRAIN | 94 | 9.4 | 7.9 | IMMATURE GRAIN | 176 | 17.6 | 14.7 |
| MILKY WHITE GRAIN | 82 | 8.2 | 6.8 | | | | |
| BROWN RICE | 20 | 2.0 | 1.8 | DAMAGED GRAIN | 26 | 2.6 | 2.3 |
| OTHER DAMAGED GRAIN | 6 | 0.6 | 0.5 | | | | |
| WHITE DEAD RICE | 13 | 1.3 | 0.6 | DEAD RICE | 24 | 2.4 | 1.1 |
| GREEN DEAD RICE | 11 | 1.1 | 0.5 | | | | |
| COLORED GRAIN | 4 | 0.4 | 0.3 | COLORED GRAIN | 5 | 0.5 | 0.4 |
| OTHER COLORED GRAIN | 2 | 0.2 | 0.1 | | | | |
| CRACKED GRAIN | 22 | 2.2 | 2.3 | CRACKED GRAIN | 22 | 2.2 | 2.3 |
| TOTAL | 1000 | 100.0 | 100.0 | TOTAL | 1000 | 100.0 | 100.0 |

| FORM AND NATURE | MATURE DEGREE | 25 |
|---|---|---|
| | EVEN GRAIN | 18 |
| | WHITE CORE WHITE BELLY | 9 |

Fig. 20

RICE QUALITY MEASUREMENT ANALYSIS RESULTS

Production District: Higashi hiroshima-shi, Hiroshima-ken  
Kind : chuseishinsenbon  
Analysis Date: 1998.5.25  
Harvest Date : 1998.10.3  
Sample No. : 0001658947

Quality Ranking: 2

| ITEM | NUMBER OF GRAINS (GRAINS) | NUMBER OF GRAIN RATIO (%) | WEIGHT RATIO (%) | ITEM | NUMBER OF GRAINS (GRAINS) | NUMBER OF GRAIN RATIO (%) | WEIGHT RATIO (%) |
|---|---|---|---|---|---|---|---|
| REGULAR GRAIN | 748 | 74.8 | 79.2 | REGULAR GRAIN | 748 | 74.8 | 79.2 |
| GREEN IMMATURE GRAIN | 94 | 9.4 | 7.9 | IMMATURE GRAIN | 176 | 17.6 | 14.7 |
| MILKY WHITE GRAIN | 82 | 8.2 | 6.8 | | | | |
| BROWN RICE | 20 | 2.0 | 1.8 | DAMAGED GRAIN | 26 | 2.6 | 2.3 |
| OTHER DAMAGED GRAIN | 6 | 0.6 | 0.5 | | | | |
| WHITE DEAD RICE | 13 | 1.3 | 0.6 | DEAD RICE | 24 | 2.4 | 1.1 |
| GREEN DEAD RICE | 11 | 1.1 | 0.5 | | | | |
| COLORED GRAIN | 4 | 0.4 | 0.3 | COLORED GRAIN | 5 | 0.5 | 0.4 |
| OTHER COLORED GRAIN | 2 | 0.2 | 0.1 | | | | |
| CRACKED GRAIN | 22 | 2.2 | 2.3 | CRACKED GRAIN | 22 | 2.2 | 2.3 |
| TOTAL | 1000 | 100.0 | 100.0 | TOTAL | 1000 | 100.0 | 100.0 |

| | | |
|---|---|---|
| FORM AND NATURE | MATURE DEGREE | 25 |
| | EVEN GRAIN | 18 |
| | WHITE CORE WHITE BELLY | 9 |

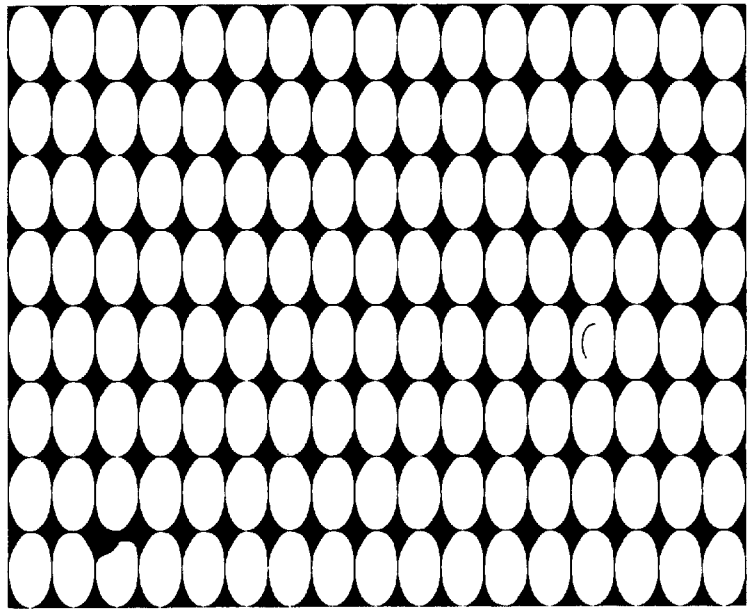

Fig. 25

APPARATUS AND METHOD FOR EVALUATING QUALITY OF GRANULAR OBJECT

BACKGROUND OF THE INVENTION (1) Field of the Invention

The present invention relates to an apparatus for evaluating quality of a granular object which analyzes the quality of the granular object such as an agricultural product, a food product and an industrial material.

(2) Description of the Related Art

For such granular objects as grains, pellets, chip-capacitors, and tablets, a quality evaluation apparatus is used to determine foreign objects or defective objects, or extent of such objects, to calculate the mixing ratio of such objects, and to determine the quality ranking of products or to set standards for quality control.

An example of the quality evaluation apparatus of grains has been disclosed in Japanese Patent Application Kokai Publication No. Hei 9-292344. The disclosed apparatus calculates the number of grains based on the quality related factors such as normal grains, immature grains, damaged or colored grains. This quality evaluation apparatus is arranged such that a disk provided at the peripheral edge thereof with a plurality of sample receiving holes is rotated, and the sample grains in the sample receiving holes are subjected, one grain at a time, to the irradiation of light, and thus the reflection light or the transmission light is received. A detection section for detecting a grain is provided above the disk, and is equipped with two light receiving elements for dividing the amount of the vertical reflection light into a long wavelength component and a short wavelength component and receiving the light for respective wavelengths, a vertical transmission light receiving element provided below the disk for receiving the vertical transmission light, a light receiving element for detecting a crack in a rice grain by receiving the slanted transmission light. The evaluation data are calculated from the amounts of light received by these four light receiving elements, and the quality of the grains, one by one, is determined based on the above evaluation data and the predetermined evaluation algorithm.

Also, there is another quality evaluation apparatus in which the image data are obtained by taking the images of a plurality of sample rice grains, the contour of individual rice grains is determined from the image data, and the quality of the rice grain is determined from the contour and the color of the image of the rice grain determined by the contour as well as the predetermined evaluation algorithm.

However, in the quality evaluation apparatus disclosed in the Japanese Patent Application Kokai Publication No. Hei 9-292344, although the grain detection section is composed of the two light receiving elements for receiving the vertical reflection light obtained by irradiating the rice grain from the light source, one light receiving element for receiving vertical transmission light, and one light receiving element for detecting a crack in a rice grain by receiving the slanted transmission light, the arrangement is such that the optical information is not obtained from both the front side and the back side of the rice grain. For example, the optical information which evaluates the quality of the rice grain, such as green dead-kernel rice grains or immature rice grains, only by the spectrum ratio of the vertical reflection light, the evaluation is made only from the data obtained from the front side of the rice grain (that is, only from the reflection light obtained from above the rice grain) and the data from the back side of the rice grain (that is, the amount of reflection light obtained from below the rice grain) has not been taken into account. Although it is rare, there are situations wherein no proper evaluation can be carried out because of an abnormal hue that appears only at the back side of the rice grain or because of the influence of the shade of the apparatus onto the rice grain.

Further, in the quality evaluation apparatus disclosed in the above publication, although the grain detection section, particularly the light receiving element for detecting a crack of a granular object is equipped with one crack detection light receiving element for receiving slanted transmission light irradiated from a slanted direction of the rice grain, no sufficient optical information is obtained at the time of the detection of the crack. The crack in the grain refers to a grain in which the crack occurs in the albumen thereof. The degrees of the cracked grains are divided into the five stages, namely, (1) a grain in which one crosswise crack runs all through, (2) a grain in which two cracks which do not run across completely are present on one crosswise surface and which, when observed from the other surface, are in two crosswise cracks, (3) a grain in which three cracks not running all through are present on one crosswise surface, (4) a grain in which any lengthwise cracks are present, and (5) a grain in which a tortoiseshell type crack is present. In this prior art example, since the optical information is taken-in by only one crack detection light receiving element, there was a possibility to overlook the crack on the other surface, or the lengthwise crack.

Also, even when the quality evaluation apparatus is with the configuration of the latter, that is, one in which the image data are obtained by taking the images of a plurality of sample rice grains, the operation in which the optical information are obtained from one side of the rice grain has failed to maintain a high precision of the quality evaluation. With this apparatus, it is impossible to achieve an accurate determination of cracks in the grains.

SUMMARY OF THE INVENTION

An object of the present invention is to overcome the above problems and to provide a quality evaluation method and an apparatus in which the data from both the front and back sides of the granular object are analyzed thereby enhancing the precision of the results of the quality analysis, especially the precision in the crack detection.

According to one aspect of the invention, there is provided a method for evaluating the quality of granular objects, the method comprising the steps of:

irradiating the granular objects selectively from a front side and a back side of the granular objects;

taking a reflection light image and a transmission light image from the front and back sides of each of the irradiated granular objects;

obtaining optical information of each of the granular objects by image-processing the reflection light image and the transmission light image;

obtaining shape information of the granular objects based on the optical information;

determining the quality of each of the granular objects based on the optical information and the shape information, the quality of granular objects including such quality as complete and incomplete granular objects;

counting the numbers of the granular objects per quality and obtaining ratios per quality of the granular objects against the total number of the granular objects;

preparing sample images of the granular objects per quality by processing the optical information; and simultaneously displaying or printing the respective numbers of the granular objects per quality, the ratios per quality of the granular objects and the sample images of the granular objects.

The sample images per quality are displayed or printed after having been arranged in a predetermined format such as a matrix form according to the respective numbers of the granular objects per quality calculated based on the ratios and the total number of the granular objects.

The method may further comprise a step of establishing a granular object quality evaluation formula based on analysis in which the quality of the granular object whose quality is known is used as objective variables and the optical information and the shape information obtained from the granular object whose quality is known are used as explanatory variables, wherein a quality for the granular objects whose quality is unknown is evaluated based on the granular object quality evaluation formula and the optical information and the shape information obtained go therefrom.

The optical information includes hue, saturation and intensity of the granular objects.

The shape information including length, width and area of the granular objects is obtained from the intensity within the optical information.

According to another aspect of the invention, there is also provided an apparatus for evaluating the quality of granular objects, the apparatus comprising:

granular object holding means formed of a material which transmits light incident thereon;

light source means for irradiating light on front and back sides of each of the granular objects held by the granular object holding means;

background means for establishing references to reflection light or transmission light from or through each of the granular objects;

image taking means for obtaining image signals of reflection light images and transmission light images from both the front and back sides of each of the granular objects, and slanted light images of one of the front and back sides of each of the granular objects;

image processing means for converting the plurality of image signals obtained by the image taking means into optical information relating to the quality of the granular objects, and converting the optical information into shape information;

arithmetic and control means for determining the quality of the granular objects per quality based on the optical information and the shape information which are obtained by the image processing means; and indicating means for displaying or printing simultaneously the results of quality evaluation obtained by the arithmetic and control means and the shape information obtained by the image processing means.

One of the light source means may comprise four separate light sources which irradiate the granular objects diagonally from four directions, the four light sources being turned on or off simultaneously or independently from each other, a plurality of the slanted light images being obtained when the four light sources are sequentially turned on.

The arithmetic and control means stores sample images of the granular objects per quality and calculates the numbers of the granular objects per quality based on the ratios of the granular objects per quality and the total number of the granular objects, arranges the order of the stored sample images according to the results of the above calculation, and outputs the results of the quality evaluation of the granular objects and the arranged sample images to the indicating means.

The arithmetic and control means stores a granular object evaluation formula obtained by analysis in which the quality of the granular object whose quality is known is used as objective variables and the optical information and the shape information obtained from the granular object whose quality is known are used as explanatory variables, and a quality of the granular object whose quality is unknown is obtained by applying the optical information and the shape information obtained from the image processing means to the granular object quality evaluation formula.

The light source means is of a circular or a ring-like shape.

BRIEF EXPLANATION OF THE DRAWINGS

The above and other objects, features and advantages of the present invention will be apparent from the following description of preferred embodiments of the invention explained with reference to the accompanying drawings, in which:

FIG. 17 is a flow chart of the granular object evaluation apparatus;

FIG. 18 is a drawing showing an example of printed quality evaluation measurement results;

FIG. 20 is an example of the quality evaluation measurement results prepared according to another flow chart and printed;

Figure 25:
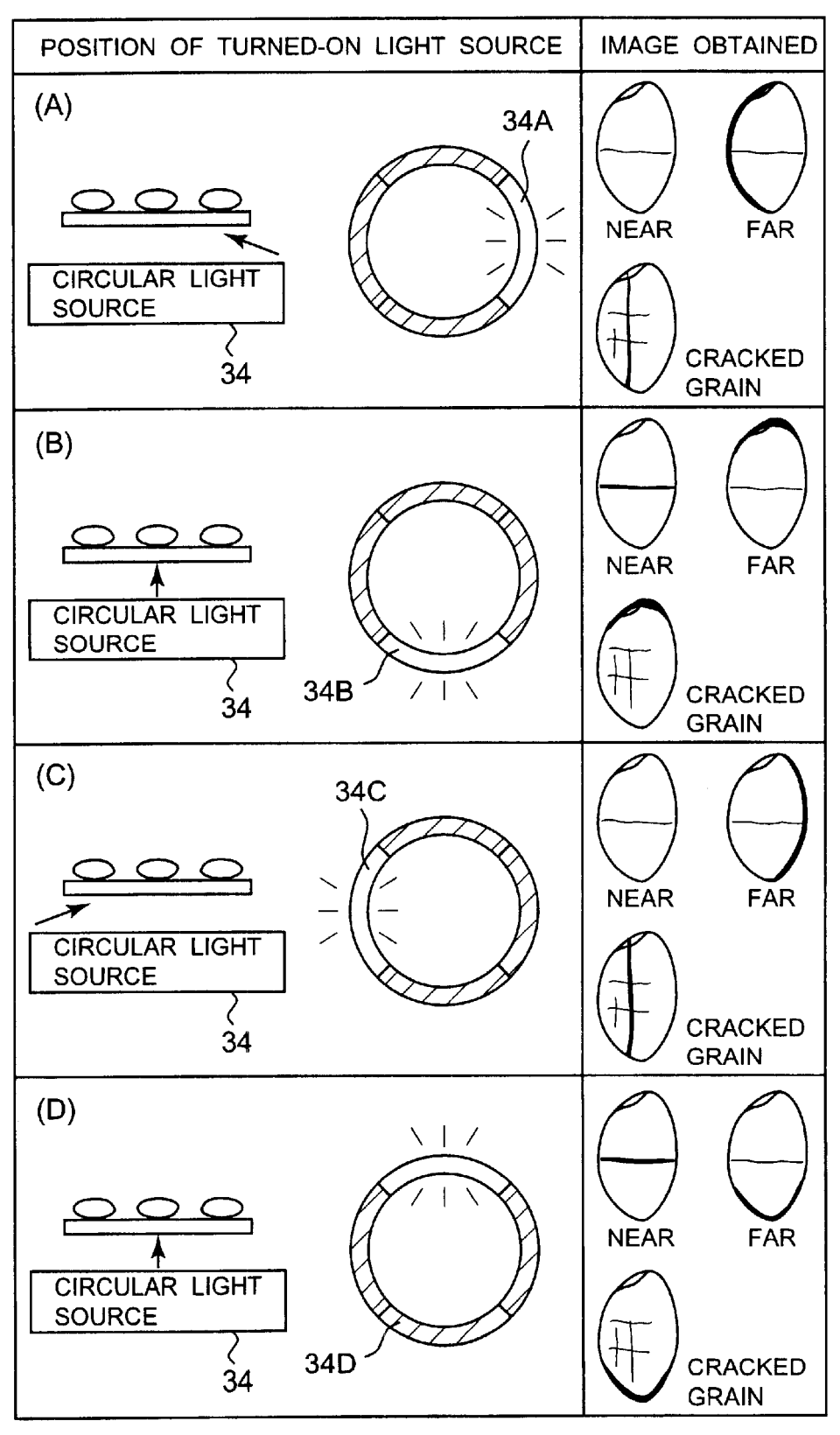

FIG. 25 is a diagram showing the states in which a plurality of arcuate light sources are selectively turned on; and FIG. 26 is a flow chart of crack detection when the plurality of arcuate light sources are selectively turned on.

PREFERRED EMBODIMENTS OF THE INVENTION

Some preferred embodiments of the present invention are explained hereunder with reference to the accompanying drawings.

Figure 1:
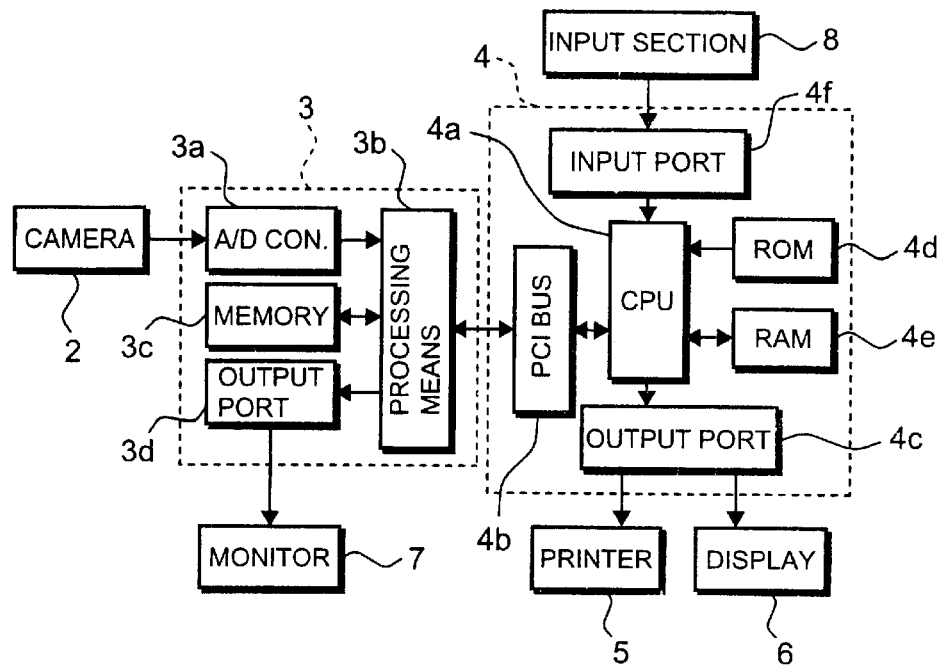
FIG. 1 is a control block diagram of the granular object quality evaluation apparatus of the first embodiment according to the invention.

FIG. 1 is a control block diagram of the granular object quality evaluation apparatus. In FIG. 1, the numeral 1 represents the granular object quality evaluation apparatus which comprises an image taking means 2 which obtains an image formed by the transmission light of the granular object and the reflection light of the granular object and which includes a camera for taking the image of plurality of sample granular objects; an image processing means 3 (e.g., "PCI bus board") which is connected to he camera of the image taking means 2 and which performs image processing, such as conversion into the optical information concerning the quality of the granular objects, of signals of the granular objects obtained through image taking by the camera; an arithmetic and control means 4 (e.g., "personal computer") which evaluates the quality of the granular objects based on the optical information obtained by the image processing means 3 and outputs simultaneously the number of objects based on the sample image and the quality of the sample granular objects and the objects ratio; a printer 5 which prints the sample-images outputted from the arithmetic and control means 4 and the number of the granular objects and the ratio of the granular objects; and a color display 6 for displaying them. The image processing means 3 may be an image processing board available on sale and, for the image processing, the arithmetic and control means 4 is equipped with an image processing application software.

As further details, the light receiving element (e.g., a 512×440 pixel area sensor) is provided in the camera which becomes the image taking means 2, and the signals of the images taken by this camera are inputted into the image processing means 3. The image processing means 3 is equipped with an A/D converter 3a which converts the inputted signals (NTSC signals) into analog signals; a processing section 3b which converts the converted digital signals into the optical information relating to qualities of the granular objects (e.g., YUV (luminance, color difference) signal and HSI (hue, saturation, intensity) signal which is further converted from the YUV signal); a memory section 3c which has a predetermined memory capacity (e.g., a capacity capable of storing about 40 sheets data of 512×512 pixels); and an output port 3d which outputs in images the optical information from the processing section 3b. A color monitor 7 is connected to the output port 3d and visibly displays the input images and the image processed by the image processing means 3. The signal processing at the processing section 3b is controlled by the image processing application stored in the arithmetic and control means 4 explained later.

The arithmetic and control means 4 is arranged such that, to the CPU (Central Processing Unit), there are connected a PCI bus 4b which is an input/output port for the image processing means 3; an output port 4c which outputs printing data to the printer 5; a memory element dedicated to reading (hereinafter referred to as "ROW") 4d in which a quality evaluation formula, programs, etc. are stored; a read and write (random access) memory element (hereinafter referred to as "RAM") 4e which stores the image processing application, image data, etc.; and an input port 4f which inputs data from the outside. To the input port 4f is connected such input means 8 as a keyboard or a touch panel. For the image processing, "Visual C++" (Trademark of Microsoft Inc.) and others can be used. When the data taken by the camera of the image taking means 2 is inputted to the signal processing section 3b of the image processing means 3, the processing section 3b of the image processing means 3 is operated by the image processing application so that the signal mode is converted from the NTSC signal to the YUV signal, and further from the YUV signal to the HSI signal. Also, the procedures such as what part of the converted signal is to be utilized for the quality evaluation data-processing are effected and controlled by a program stored in the ROM 4d separately from the image processing application.

Figure 2:
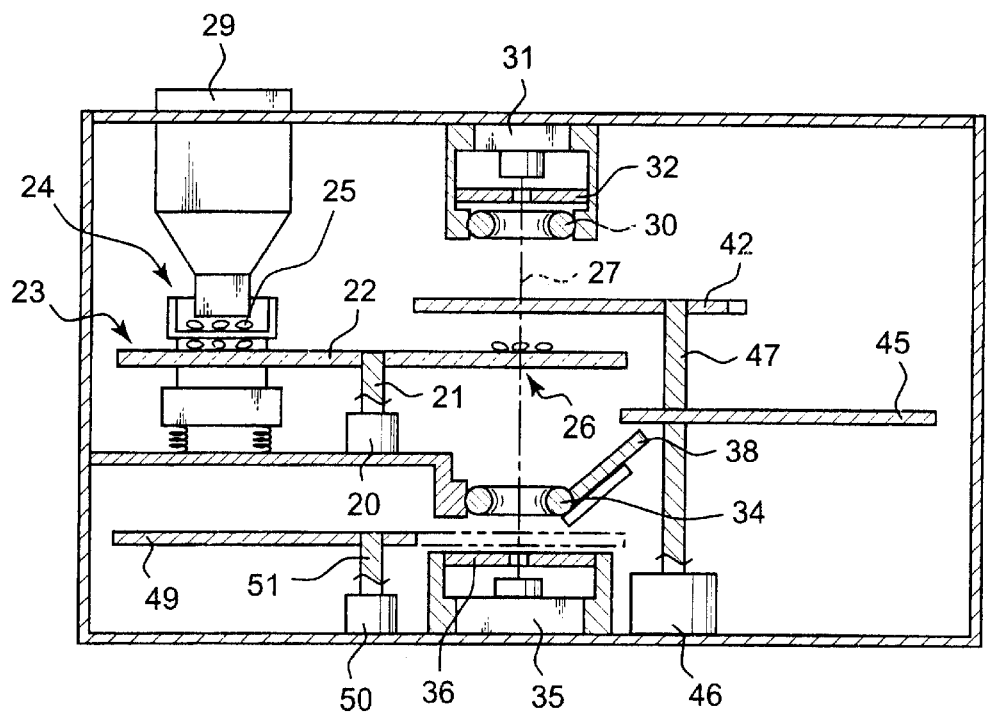
FIG. 2 is a diagrammatic side sectional view showing an internal arrangement of a measuring section provided of an image taking means.
Figure 3:
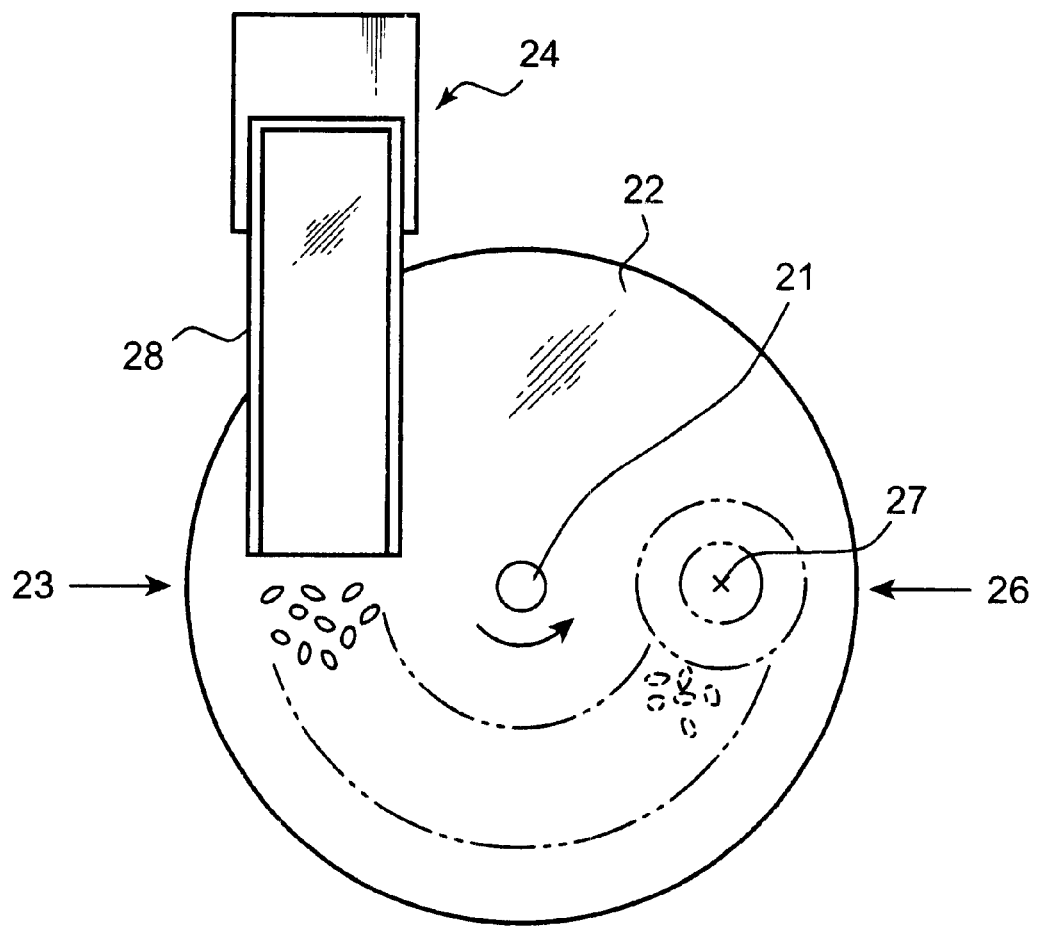
FIG. 3 is a plan view of a feeder and a granular object holding means.

Next, the measuring section provided at the image taking means 2 is explained with reference to FIGS. 2 to 5. FIG. 2 is a diagrammatic sectional view showing an internal arrangement of the measuring section provided at the image taking section. FIG. 3 is a plan view showing the feeder of the measuring section and the granular object holding means. It is shown particularly that the granular object holding means is in the form of a glass disk. As shown in FIGS. 2 and 3, the measuring section consists mainly of a circular disk 22 rotated by being supported by a rotary axis 21 of a stepping motor 20; a feeder means 24 (hereinafter referred to as "feeder") provided at one peripheral portion 23 of the rotary disk 22; and an image taking point 26 of the image taking means 2 provided at another peripheral portion of the rotary disk 22. The feeder 24 is provided with a hopper 29 which holds the sample granular objects at a position above a trough 28, and the granular objects supplied at one portion of the rotary disk 22 from the hopper 29 through the feeder 24 are transferred to the image taking point 26 at the other portion by the rotation of the motor 20.

Figure 4:
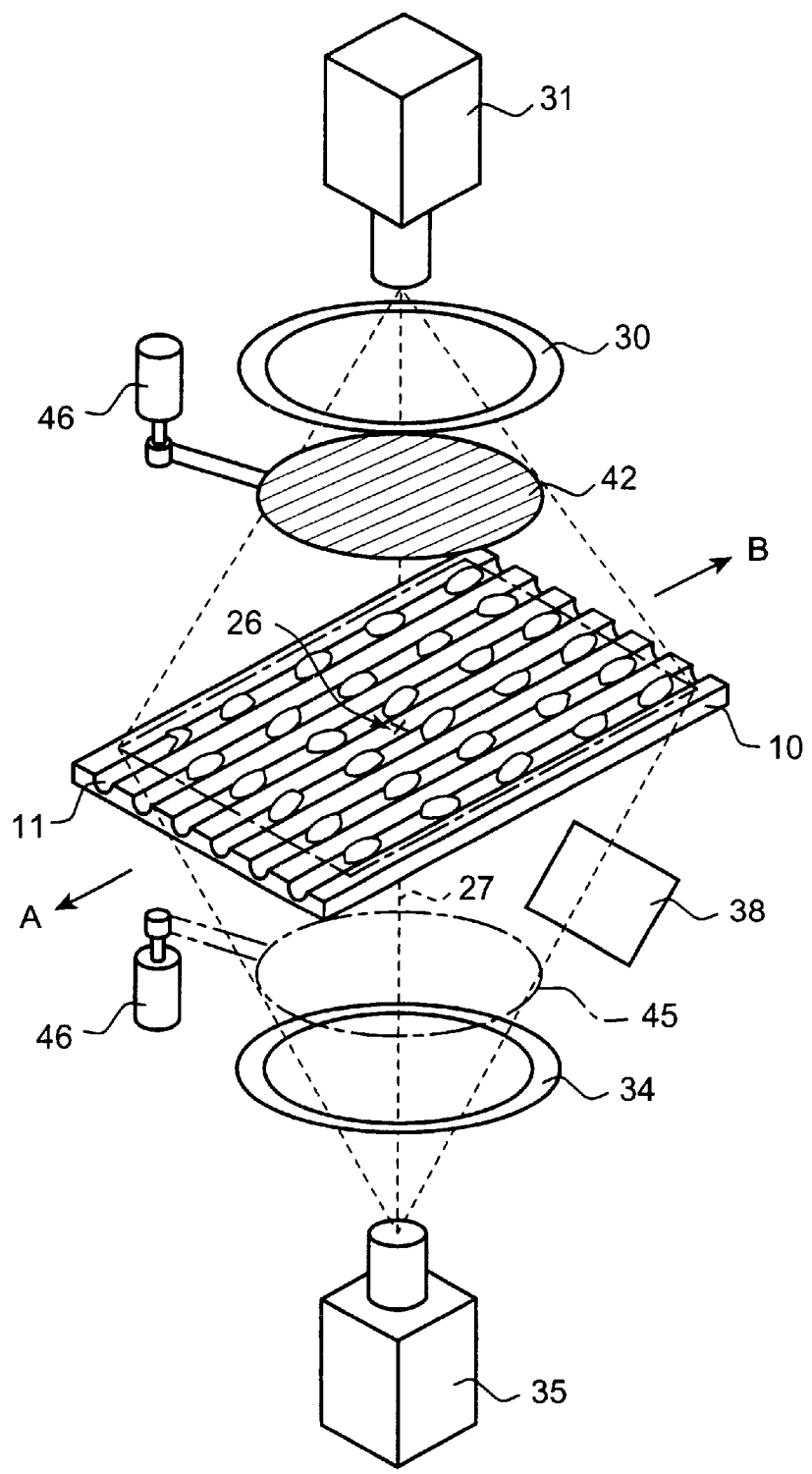
FIG. 4 is a diagrammatic perspective view showing another example of the granular object holding means.

FIG. 4 is a diagrammatic perspective view showing another embodiment of the granular object holding means, in which the granular object holding means is in the form of a slide plate. The slide plate 10 is formed of a material which transmits light from the light source, for example, an acrylic resin material, and is provided with a plurality of grooves 11 which cause the granular objects to be aligned in a plurality of rows in a single layer state. Granular objects are supplied to the slide plate 10 by the feeder means 24, and it is preferred for the bottom surface thereof to have the same grooves as in the slide plate 10. When the measuring operation starts, the slide plate 10 moves in the direction of arrow A and each of the granular objects moves to the image taking point 26. Upon completion of the measuring operation, the slide plate 10 moves further in the direction of arrow A, the granular objects are discharged, the empty slide plate 10 moves in the direction of arrow B, and the new granular objects are supplied thereon.

When it is arranged such that the granular objects on the slide plate 10 provide a plurality of image signals through the image taking means, it is possible to provide the image signals of the granular objects in a state in which the image signals of the granular objects are orderly lined-up on the slide plate 10. Thus, as compared with irregular image signals of the granular objects, the well-ordered image signals have better appeal to the eyes.

Referring to FIGS. 2 and 4, in the imaging taking point 26, the image taking viewing line 27 is positioned vertically to the rotary disk 22 or to the slide plate 10 and, above the image taking viewing line 27, there are provided a light source 30 of the circular type, a camera 31, and a slit 32 (not shown in FIG. 4) positioned between the camera 31 and the light source 30. On the other hand, below the image taking viewing line 27, there are similarly provided a light source 34, a camera 35, and a slit 36 (also not shown in FIG. 4). The camera 31 and the camera 35 take images of the granular objects supplied onto the image taking point 26 through respectively the slits 31 and 36 and irradiated by the light sources 30 and 34. Further, in this embodiment, at the side of the light source 34, there is provided a surface light source 38 which irradiates the granular objects on the rotary disk 22 in a slanted angle. It is preferred that the light sources 30, 34 and 38 be LEDs, and their wavelength regions be visible regions of 420–700 nanometers.

Figure 5:
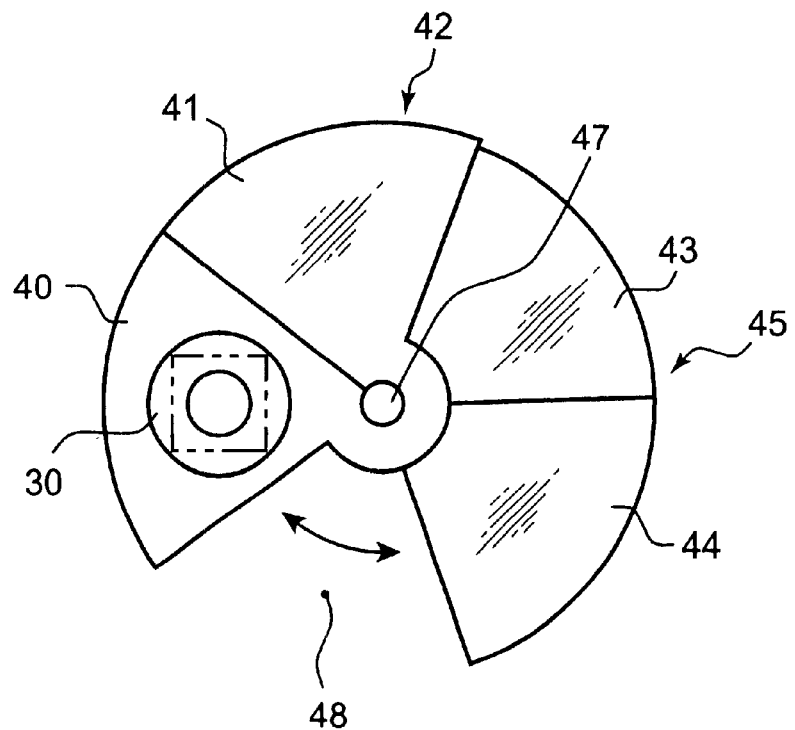
FIG. 5 is a plan view of a background plate and shows a position and a rotating state thereof.
Figure 6:
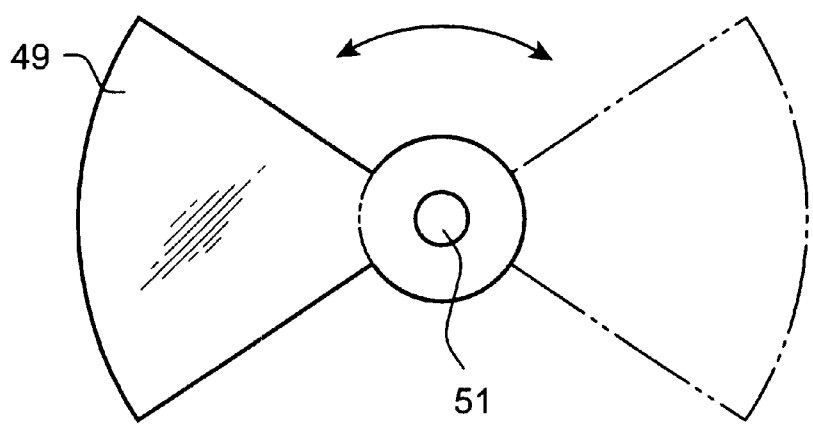
FIG. 6 is a plan view of a background plate and shows a position and a rotating state thereof.

Next, the background plate means is explained with reference to FIGS. 2 and 5. FIG. 5 is a plan view showing the structural arrangement of the background means provided at the measuring section. Between the image taking point 26 and the light source 30 at the measuring section, there is selectively inserted a background plate 42 for blocking the viewing line 27 and, between the image taking point 26 and the light source 34, there is selectively inserted a background plate 45 for blocking the viewing line 27. The background plate 42 is integrally formed of two kinds of plates, one being a milky white plate 40 and the other being a black plate 41. Similarly the background plate 45 is integrally formed of two kinds of plates, one being a milky white plate 43 and the other being a black plate 44, and the background plate 42 and the background plate 45 are freely interchangeable. That is, as shown in FIG. 5, the background plates 42 and 45 are supported by the rotary axis 47 of the stepping motor 46, and the rotation of the motor 46 enables the changing among the background plate 42 (milky white plate 40 and black plate 41), the background plate 45 (milky white plate 43 and black plate 44), and no background plate 48. FIG. 6 is a plan view showing the structural arrangement of the background means provided at the light source 34. Between the light source 34 and the slit 36, there is inserted interchangeably a background plate 49 which is made up of the black plate for blocking the viewing line 27 and which rotates by being supported by the rotary axis 51 of the stepping motor 50.

Figure 7:
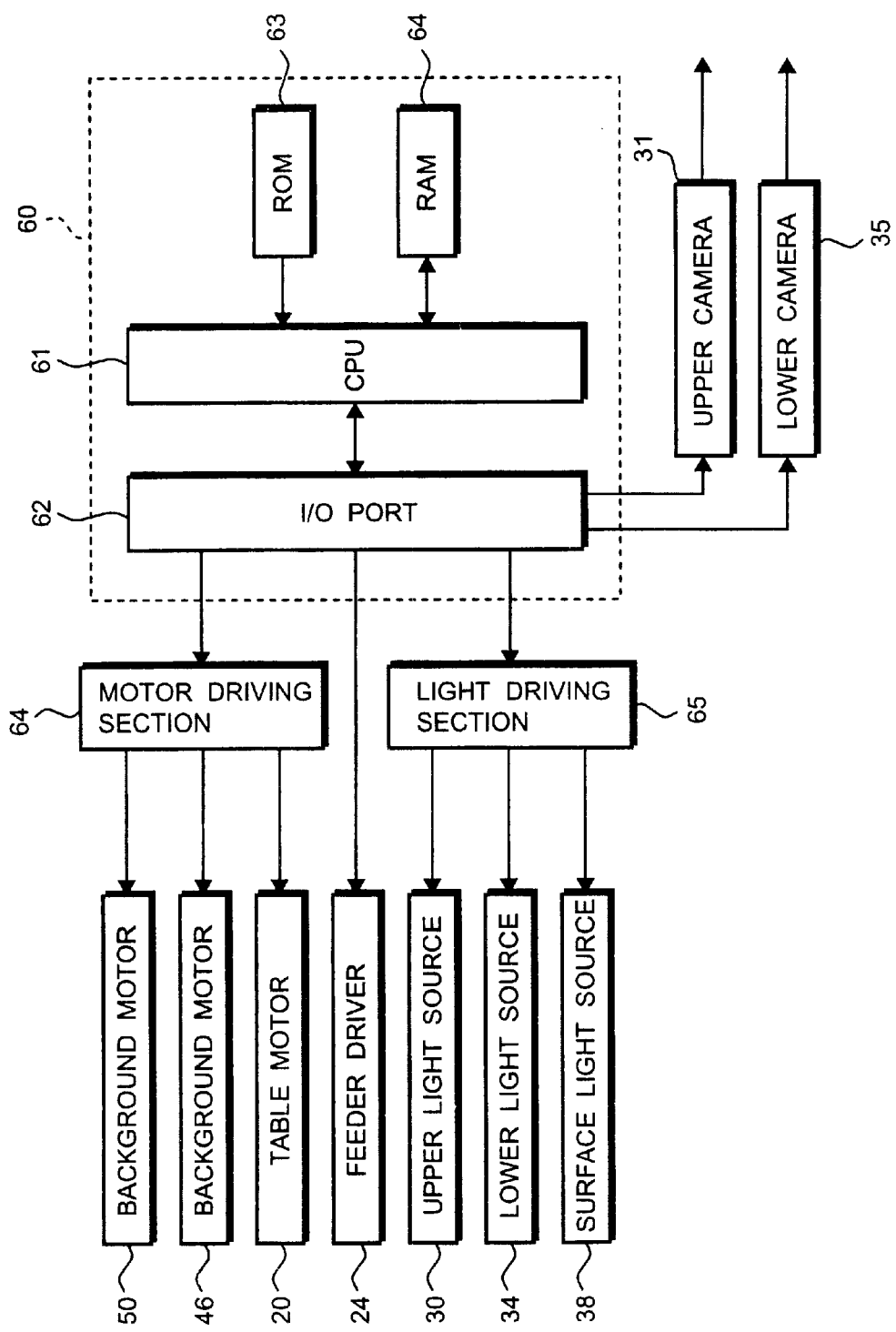
FIG. 7 is a control block diagram of the image taking means.

Next, the control means for the above image taking means 2 is explained. FIG. 7 is a block diagram showing a control means 60 for the image taking means 2. The control means 60 shown in FIG. 7 is arranged such that, with the CPU 61 being as a main component, there are connected an input/output port 62, a read-out memory element (ROM) 63, and a read and write memory element (RAM) 64. Connected respectively to the input/output port 62 are a motor driving section 64, a feeder driving section 24, and a light source driving section 65, and connected further to the input/output 62 are an upper camera 31 and a lower camera 35. Also, to the motor driving section 64, there are connected a rotary disk motor 20, a background plate motor 46, and a background plate motor 50. Each of these motors 20, 46, 50 receives instructions from the CPU 61 through the programs stored in advance in the ROM 63 and the rotation of each of them is controlled. Also, in this embodiment, to the above light source driving section 65, there are connected an upper light source 30, a lower light source 34, and the surface light source 38 to irradiate in a slanted angle. The CPU sends instructions through the programs stored in advance in the ROM 63, and each of the light sources 30, 34, 38 are ON/OFF controlled. The upper camera 31 and the lower camera 35 take images according to the instructions from the control means 60, and the image data taken by the image taking operations is sent to the image processing means 3 according to the instructions from the control means 60.

Figure 8:
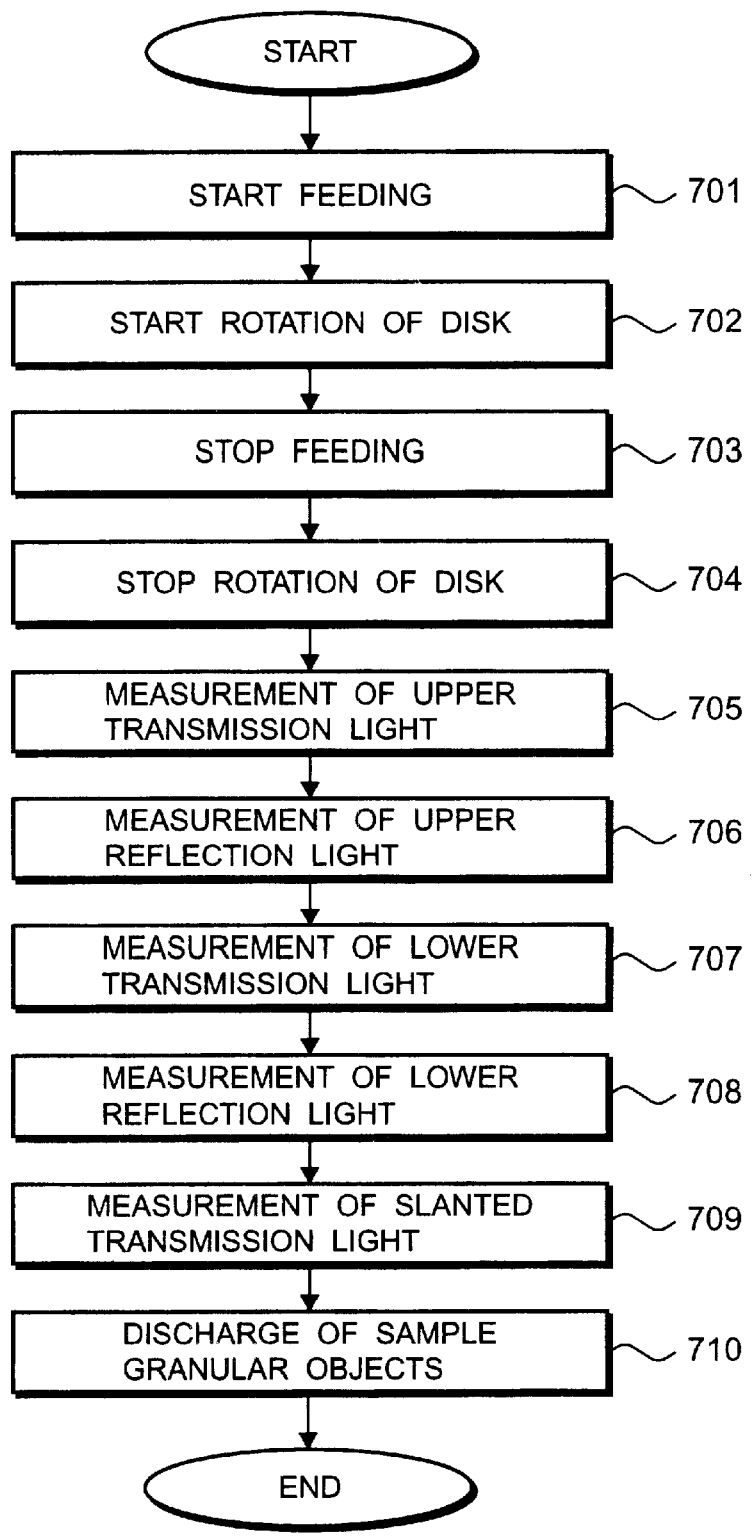
FIG. 8 is a flow chart of the image taking means.

In the ROM 63 shown in FIG. 7, the program as shown in the flow chart of FIG. 8 is stored. Specifically, first, when the sample granular objects are introduced from the hopper 29 shown in FIG. 2 and the measuring is started, the feeder 24 is driven (step 701), the motor 20 is rotated (step 702), and the granular objects are supplied in a layer form from the feeder 24 to the rotary disk 22. When the granular objects are supplies up to the predetermined amount in a layered form onto the rotary disk 22, the feeder 24 is stopped (step 703) and, upon the granular objects reaching the image taking point 26, the rotary disk stops (step 704). In this regard, please see FIG. 3.

The measuring of the upper transmission light is conducted by rotating the background plate motor 46 a predetermined amount and the milky white plate 43 is moved to the position of the viewing point 27, turning ON the lower side light source 34, and taking an image (step 705) of the transmission light from the granular objects by the upper camera 31 from above. Then, the image data is sent to the image data processing means 3 (in the image data obtained then, the images of about 450 granular objects, for example, are present).

The measuring of the upper reflection light is conducted by rotating the background plate motor 46 a predetermined amount and the black plate 44 is moved to the position of the viewing point 27, turning OFF the light source 34 and turning ON the upper light source 30, and taking an image (step 706) of the reflection light of the granular objects by the upper camera 31 from above. Then, the image data is sent to the image processing means 3.

Similarly the measuring of the lower transmission light is conducted by rotating the background plate motor 46 a predetermined amount and the milky white plate 40 is moved to the position of the viewing point 27, turning ON the upper light source 30, and taking an image (step 707) of the transmission light of the granular objects by the lower camera 35 from below. Then, the image data is sent to the image processing means 3.

Also, similarly, the measuring of the lower reflection light is conducted by rotating the background plate motor 46 a predetermined amount and the black plate 41 is moved to the position of the viewing point 27, turning OFF the light source 30 and turning ON the lower light source 34, and taking an image (step 708) of the reflection light of the granular objects by the lower camera 31 from below. Then, the image data is sent to the image processing means 3.

Finally, in this embodiment, the measuring of the slanted transmission light is conducted by rotating the background plate motor 46 a predetermined amount and no background plate 48 is moved to the position of the viewing point 27, rotating the background motor 50 a predetermined amount and moving the black plate 49 to the position of the viewing point, switching ON the surface light source 38, and taking an image (step 709) of the slanted transmission light of the granular objects by the upper camera 31 from above. Then, the image data is sent to the image processing means 3.

When the image taking of the five images from the step 705 to the step 709 has been completed, the motor 20 for the rotary disk 22 is rotated by a predetermined amount, and the granular objects having undergone the image taking are discharged by the discharging means (not shown) and the measuring is terminated (step 710). It is preferable that the arithmetic and control means 4 performing data processing be electrically communicated with the control means 60 performing the image taking timing of the cameras and, if the program is stored such that the operation of the steps 705–709 is repeatedly carried out according to the image data requesting signals from the arithmetic and control means 4, the obtaining of the images may be automated.

The image data of the step 705 to the step 709 are sent to the image processing means 3, and are image-processed following the programs stored in the ROM 4d of the arithmetic and control means 4.

Figure 9:
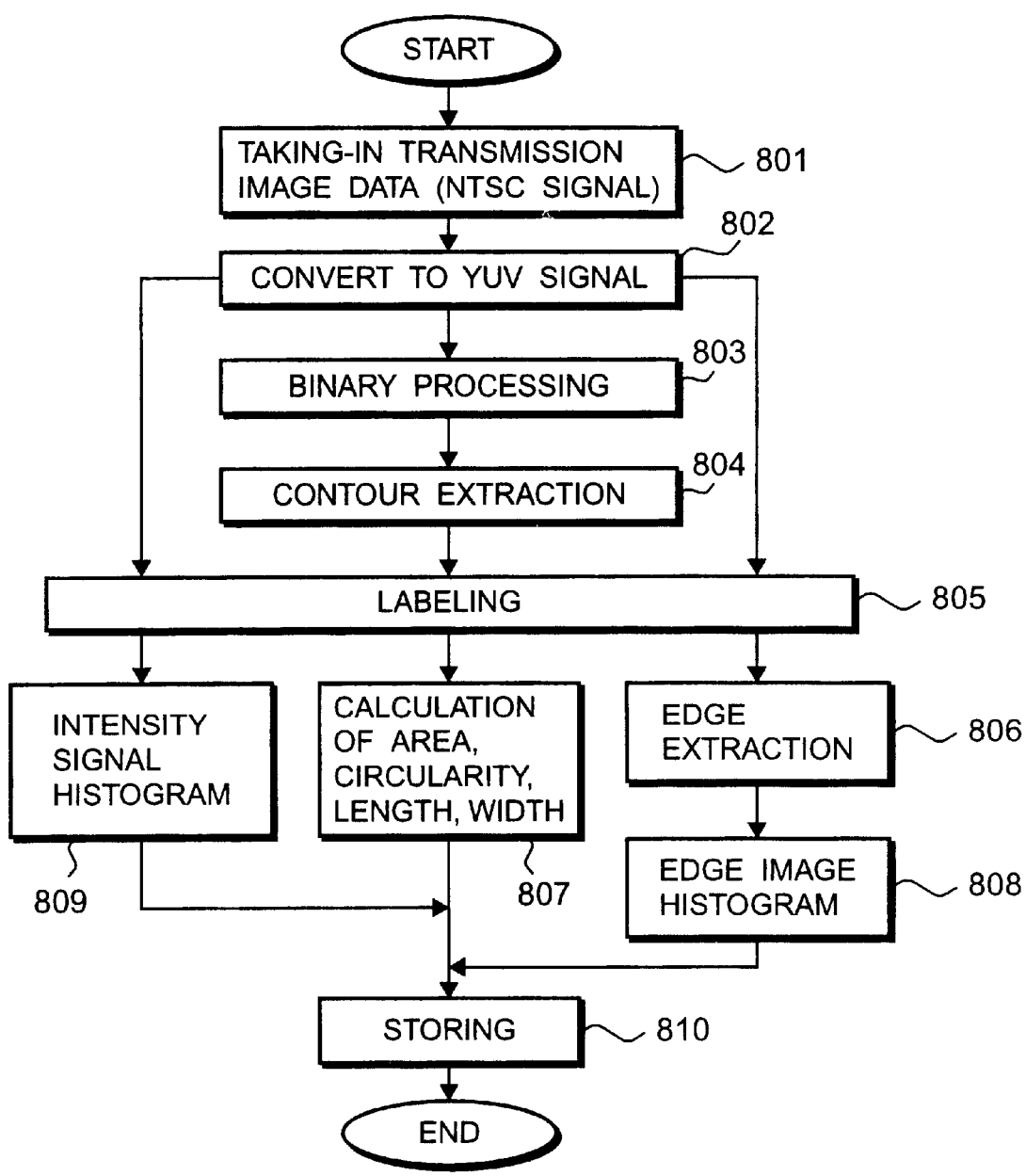
FIG. 9 is a flow chart of processing the image data of the transmission light.
Figure 10:
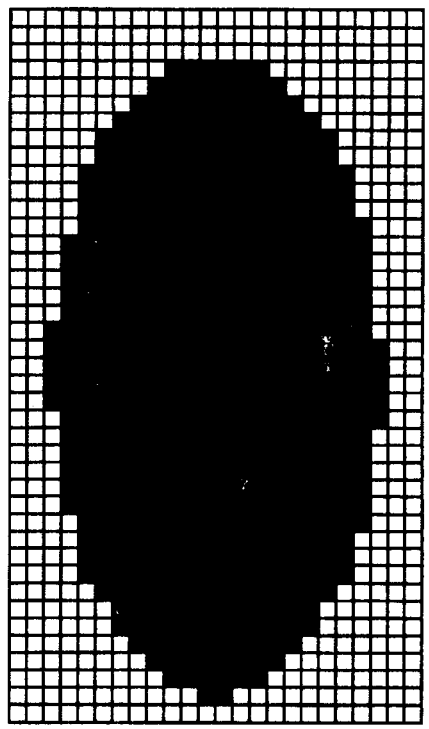
FIG. 10 is a drawing showing an example of the image obtained by binary processing of the transmission light image data.

Next, the image processing of the image data by the transmission light shown in step 705 and step 707 is explained with reference to FIG. 9. FIG. 9 shows an image processing flow chart, and the arithmetic and control means 4 instructs that the transmission image data (NTSC signals) of the image taken sample granular objects be taken-in (step 801), and the transmission image data (NTSC signals) be converted to YUV (luminance, color difference) and be stored in the memory section 3c (step 802). Next, the arithmetic and control means 4 instructs that, by using the luminance signal within the YUV signals (luminance, color difference) of the memory section 3c, the binary process be conducted (step 803) for each image element with the predetermined threshold value being used as reference. Since, by the binary process, the contours of the granular objects can be grasped as shown in FIG. 10, the process of extracting the contours of the granular objects is instructed (step 804). The image data contain data of a plurality of granular objects, and each granular object is labeled by an identification symbol (step 805)

Figure 11:
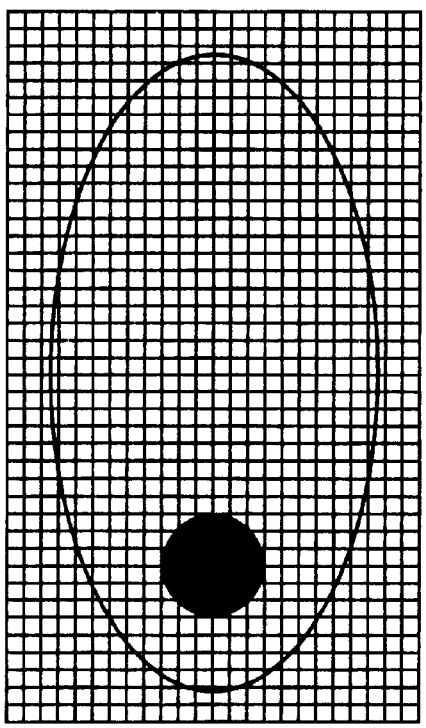
FIG. 11 is a drawing showing an example of the transmission light image data prior to the image processing.
Figure 12:
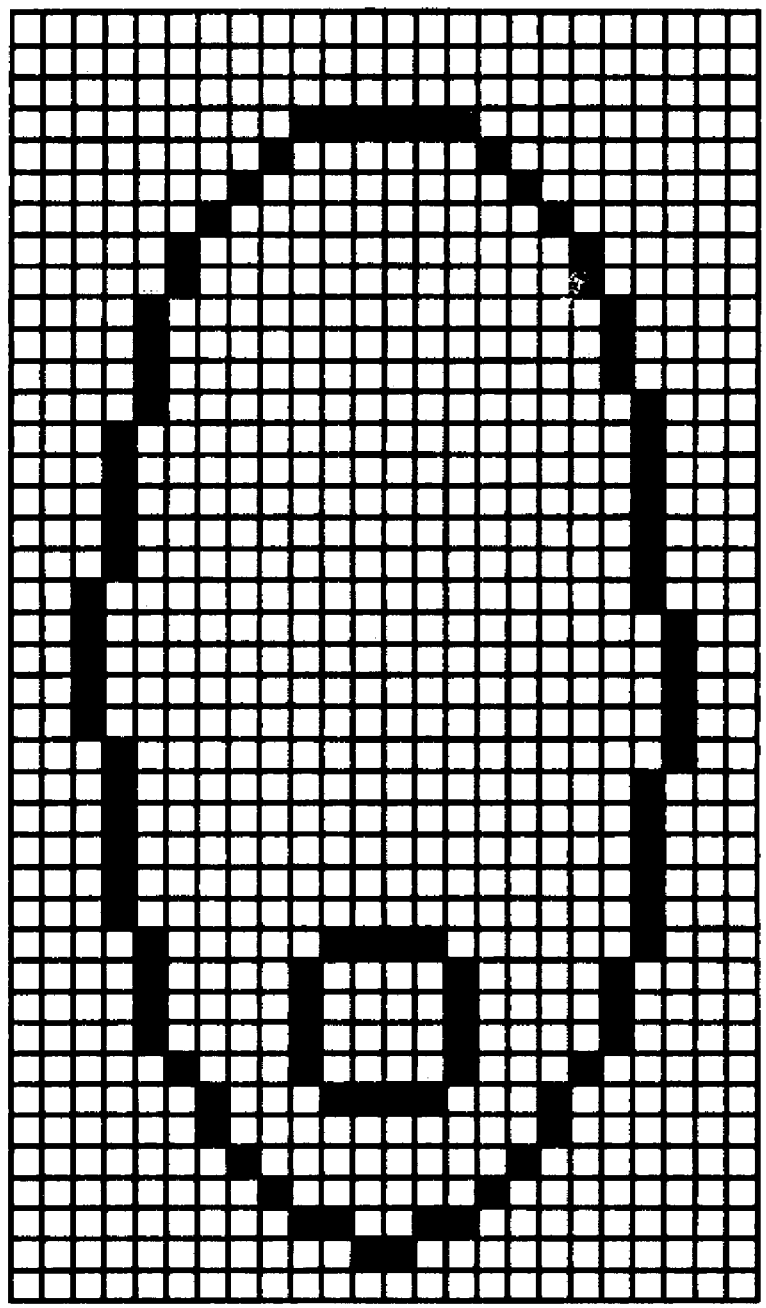
FIG. 12 is a drawing showing an example of the image obtained by edge processing of the image.

When the contour of the granular object is obtained, the area of the granular object is derived from the number of image elements (pixels) within the contour, and the major axis and the minor axis of the diagram are determined by the image processing, thus enabling to specify the width and the length of the object (step 807). Further, by using the luminance signal within the YUV signals (luminance and color difference), it is instructed that the edge image be extracted from the luminance (step 806). The edge image is an image obtained by subjecting the luminance (brightness) signal to the differential process, and processed such that the gradient portion of the luminance (brightness) is taken out as a signal. For example, as in FIG. 11, in the cases as when a color appears at a portion of the granular object, or an opaque portion appears in the endoplasm thereof, there exists a gradient portion in the luminance (brightness) in the contour of the granular object, or in the boundary portion with respect to other colors. When they are subjected to the edge image processing, the processed images as shown in FIG. 12 can be taken out. Next, in order to extract the features of the granular objects, the histogram of the edge image signal for each granular object is prepared (step 808) from the edge image with respect to the luminance (brightness) of each image element.

It is instructed that, from the luminance (brightness) signal itself, the histogram of the luminance (brightness) signal be prepared for each granular object (step 809).

The contour of the granular object obtained by the step 807 is used as the shape information, and the YUV (luminance, color difference) signal, the luminance (brightness) signal, the histogram of the edge image obtained by the step 808, and the histogram of the luminance signal obtained by the step 809 are used as optical information. The above five feature items are stored (step 810) within the labels corresponding to individual granular objects in the RAM 4e of the arithmetic and control means 4. From the image data through the transmission light, the diffusion light transmitted through the milky white background plate is detected as light having relations with the shape of the granular object and the endoplasm. By the detection of the shape of the sample granular object and the amount of the transmission light, it is possible to obtain the feature relating to the shape of the granular object. The luminance signal processed here may be monochrome signal.

Figure 13:
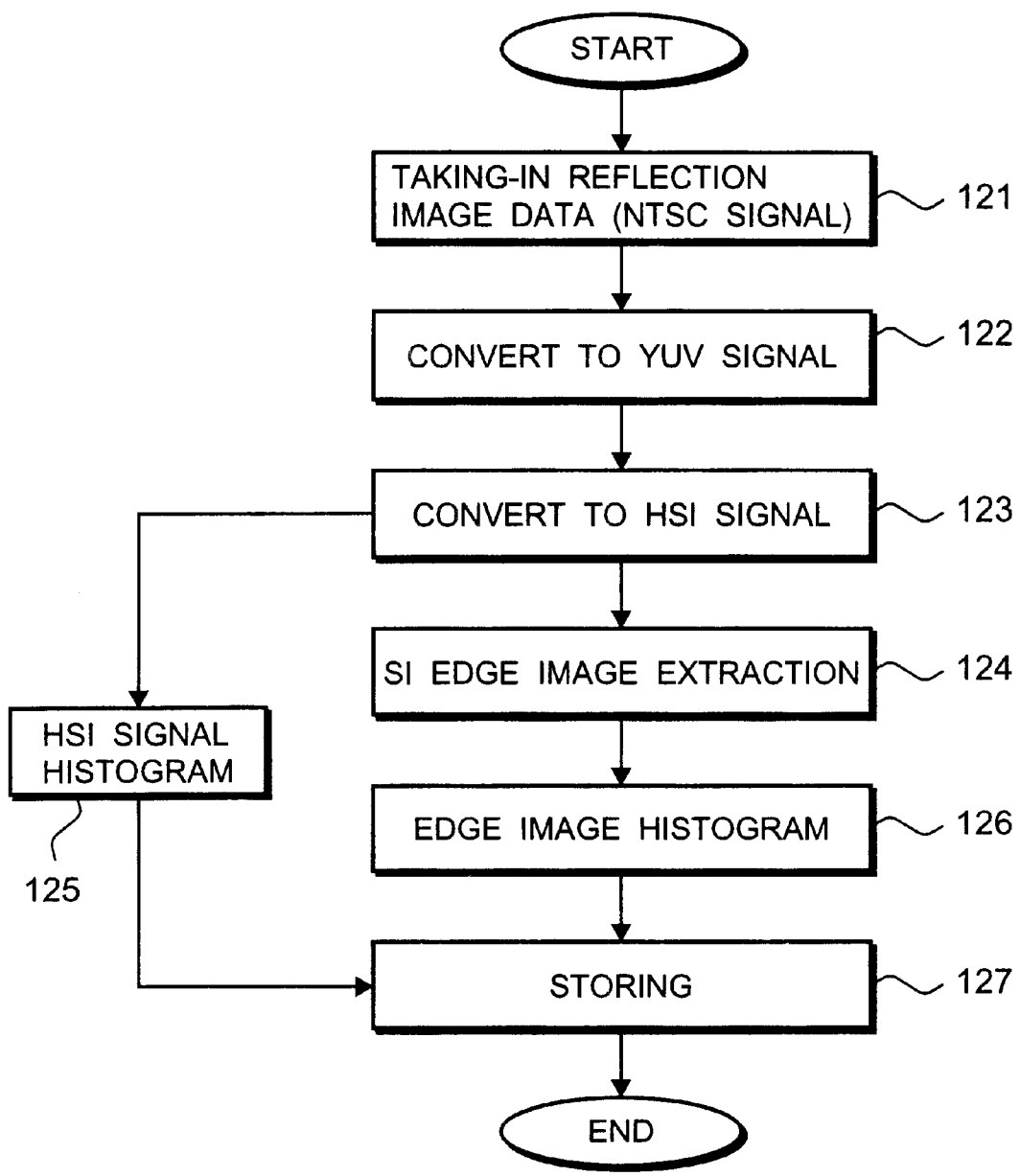
FIG. 13 is a flow chart of the image data processing of the reflection light.

Next the image processing of the image data from the reflection light shown in the step 706 and the step 708 is explained with reference to FIG. 13, which is a flow chart showing the image processing. The arithmetic and control means 4 instructs that the reflection image data (NTSC signal) of the image taken from the sample granular object be taken-in (step 121) and the reflection image data (NTSC signal) be converted (step 122) to the YUV (luminance, color difference) and be stored in the memory section 3c. Then, the arithmetic and control means 4 instructs that the YUV (luminance, color difference) signal in the memory section 3c be converted to the HSI (hue, saturation, intensity) signal and be stored (step 123). Next, the arithmetic and control means 4 instructs that the SI (saturation, intensity) signal be taken out and the edge image be extracted (step 124). The contents of edge image are as already explained. It is also instructed that, in order to extract the features of the granular object, the histogram of the HSI (hue, saturation, intensity) signal be prepared from the HSI (hue, saturation, intensity) signal, the histogram of the edge image be prepared for each granular object (step 125). Here, the histogram of the YUV (luminance, color difference) signal, the HSI (hue, saturation, intensity) signal, and the histogram of the HSI signal obtained by step 125, and the histogram of the edge image of the SI (saturation, intensity) signal obtained by step 126 are used as optical information. The above four feature items are stored in the RAM 4e of the arithmetic and control means 4. At this time, by using the label which was attached in the transmission image processing, the storing may be made within the label for each granular object. Also, separately from the transmission image processing, the label for the reflection image processing may be attached, and the data as corresponding to the same granular object may be stored. That is, from the reflection light obtained from the granular object with the background being the black plate, the light having relations to colors of the granular object is detected and, by detecting the reflection light of individual sample granular objects, the feature of the granular object concerning the colors can be obtained. The signal here is a color signal.

Figure 14:
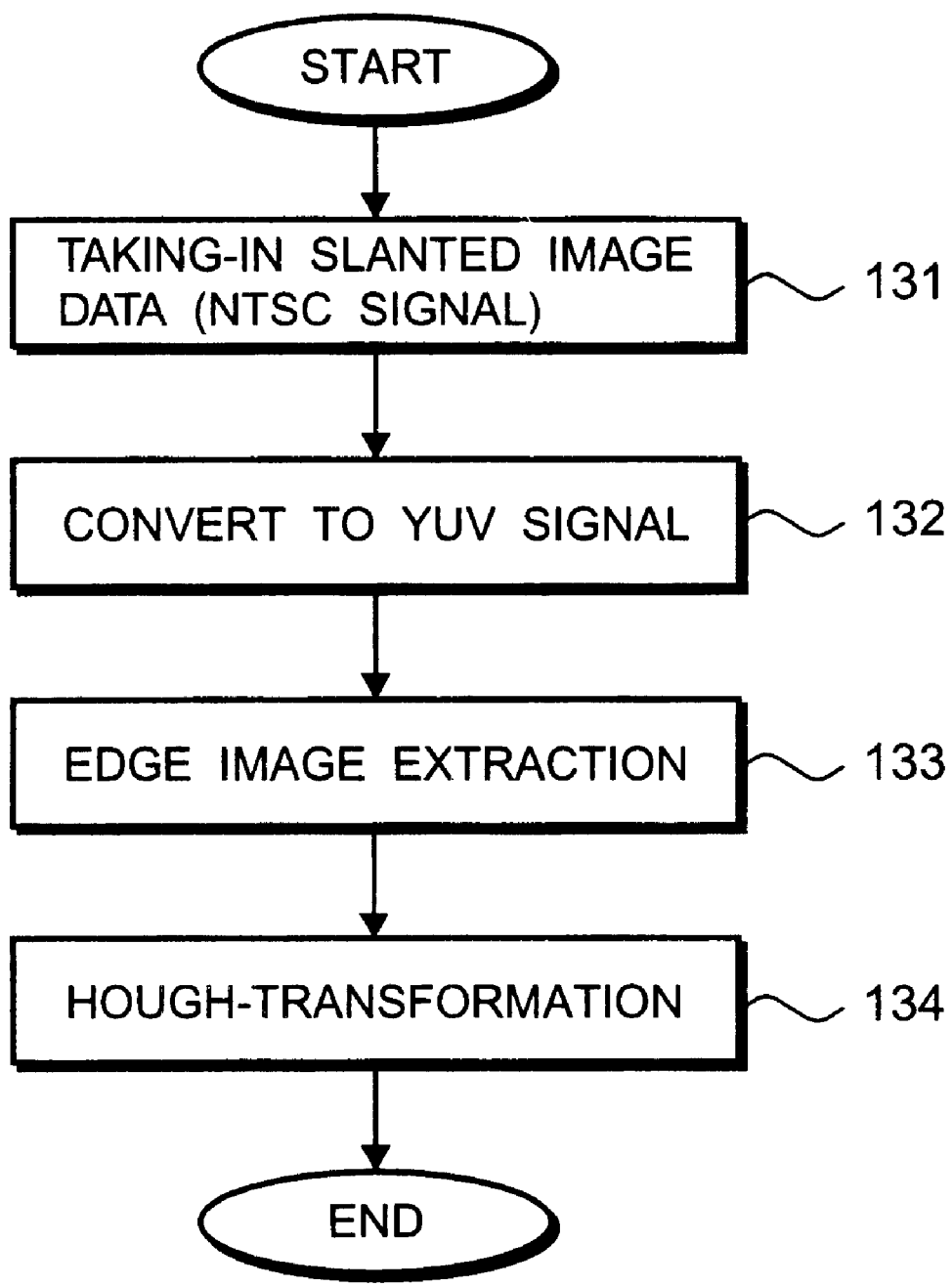
FIG. 14 is a flow chart of the image data processing of the slanted light.
Figure 15:
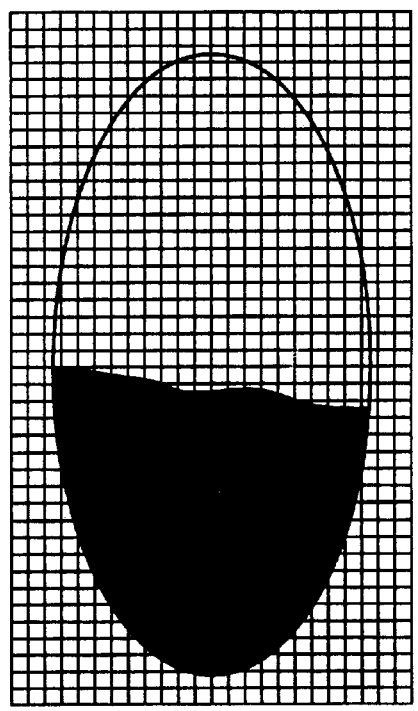
FIG. 15 is a drawing showing an example of the slanted light image data prior to the image processing.
Figure 16:
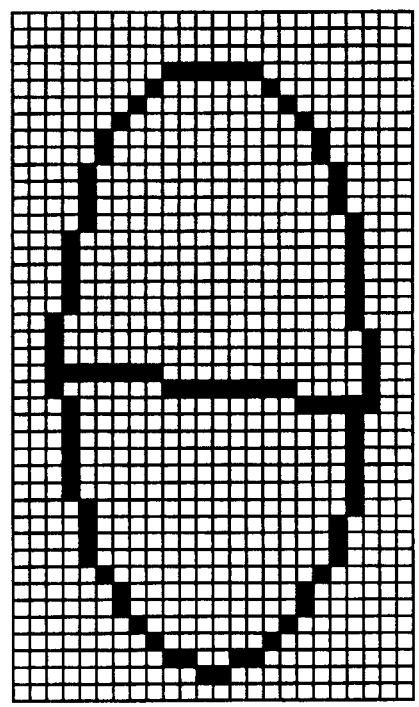
FIG. 16 is a drawing showing an example of the image obtained by image processing of the slanted light image.

Now, in this embodiment, the image processing of the slanted transmission image data is explained with reference to FIGS. 14 to 16. FIG. 14 is a flow chart of the image processing. The arithmetic and control means 4 instructs that the slanted light image data (NTSC signal) having undergone the image taking be taken-in (step 131) and the slanted light image data (NTSC signal) be converted to the YUV (luminance, color difference) and be stored in the memory section 3c (step 132). Then, the arithmetic and control means 4 extracts the edge image (step 133) by using the luminance signal within the YUV (luminance, color difference) signals. This is explained with reference to FIG. 15. With respect to the granular object in which a crack has occurred inside thereof, if the slanted light irradiates substantially perpendicularly to the crack surface, the irradiated side of the light is seen bright while the other side is seen dark with the crack surface being the boundary. At this point, when the edge image resulted from the differential processing concerning the luminance (brightness) is extracted, the crack portion is extracted, as shown in FIG. 16, as cross sectional (or vertical sectional) lines of the granular object. Next, for the features of the granular object to be extracted, the arithmetic and control means 4 instructs that the edge image be Hough-transformed to specify the lines resulting from the crack (step 134). Here, the YUV (luminance, color difference) signal, the edge image obtained by step 133, and the value obtained by step 134 and Hough-transformed becomes the optical information. The above three feature items are stored in the RAM 4e of the arithmetic and control means 4. At this time, the label for each individual grain may be one corresponding to the label attached when the transmission images are processed.

In the image data by the transmission light, reflection light, and slanted light as explained above, the obtaining of reference data by reference plate serving as reference has been omitted. However, when the luminance of the reference plates or the images are taken-in in advance as reference data, it is possible to correct each image data, and more specifically, to balance the luminance or colors of the background plates serving as backgrounds.

For the quality evaluation of the granular objects, the ROM 4d shown in FIG. 1 stores in advance the grain quality related or evaluation formula. This formula is one obtained, for example, in the following ways. From the granular object whose quality and/or crack is known, the area ($X_1a$), a circularity degree ($X_2a$), a length ($X_3a$), and a width ($X_4a$) of the granular object, a histogram ($X_5a$) of the edge image signal of the granular object, a histogram ($X_6a$) of the luminance signal of the granular object, a histogram ($X_7a$) of the HSI signal of the granular object by the reflection image, a histogram ($X_8a$) of the edge image of the granular object, and the signal ($X_9a$) Hough-transformed of the edge image of the granular object by the slanted image are obtained. By using such information as explanatory variables ($X_na$) and a complete granular object ($T_1$), incomplete granular object ($T_2$) and, in the case of grains, a regular grain ($T_3$), an immature grain ($T_4$), a dead grain ($T_5$) etc. as objective variables ($T_a$) a linear analysis such as a multiple regression analysis is performed as follows:

$$T_a = F_0 + F_1 \cdot X_1 a + F_2 \cdot X_2 a + F_3 \cdot X_3 a + F_4 \cdot X_4 a + F_5 \cdot X_5 a + F_6 \cdot X_6 a + F_7 \cdot X_7 a + F_8 \cdot X_8 a + F_9 \cdot X_9 a + c$$

Here $T_a$ is an objective variable representing the qualities of granular object such as a regular grain, an immature grain or a dead grain.

$F_{0-F9}$ is a coefficient value.

$X_1 a \sim X_9 a$ is an explanatory variable obtained from the optical information.

Apart from the above, by the non-linear analysis such as neural network, the granular object quality related formula for obtaining the quality of the granular object whose quality is unknown may be prepared. That is, with respect to the granular object whose quality is unknown, it is possible to determine the quality by the information obtained based on the transmission light image, the reflection light image, or slanted light image and on the granular object quality related formula. The information referred to above is only an example, and it is not the condition that all the information is required to be used. As to the linear analysis and the non-linear analysis, a known method of analysis is available for use.

Further, the control program as a whole of the arithmetic and control means 4 after the image processing is explained with reference to FIG. 17, which is a control flow chart of the arithmetic and control means 4. First, an image data of the same granular object is obtained (step 161) by the camera 2, and is converted to an image data acceptable for processing and is stored in the memory section 3c (step 162). The image data thus obtained is image processed (step 163) for each granular object as explained above by the arithmetic and control means 4 and the image processing means 3, thus providing the shape information and the optical information having been image processed of, for example, 450 granular objects. By using the shape information, the optical information, and the granular object quality related formula, the quality of the granular objects on a label to label basis is calculated and specified (step 164) and the number of granular objects is calculated on a quality to quality basis (step 165). Further, the ratio of the number of granular objects on a quality to quality basis is calculated (step 166). The image data for each granular object is obtained by dividing the signal obtained by the processing of the reflection image data, for example, the YUV (luminance, color difference) signal, and the image processing means is instructed to store such data in the memory section 3c (step 167). In the image processing, the contour of each granular object is determined by the transmission light image data as already explained and, based on this contour, the reflection light image data of the same label is divided for each granular object, and finally they may be re-arranged in a matrix form. Where the sample images are prepared by utilizing the reflection light image data, the color becomes clear and thus assists the visual aspect. By the arithmetic and control means 4, the ratio of the number of the granular objects for each quality obtained and the image data (for example, for 450 granular objects) for each granular object are simultaneously outputted in a predetermined format from the output port 4c to the color printer 5 or the color display 6 (step 168). FIG. 18 shows, as one example of the print out, the completed quality evaluation data of the granular objects. As above, according to the embodiment of the invention, in addition to the number of granular objects and the ratio of the number of granular objects on a quality to quality basis, the sample images of the sample granular objects obtained as images can also be provided. In this way, by the image data of the sample granular objects, the quality evaluation is made possible and, in addition, the sample images can be prepared.

Figure 19:
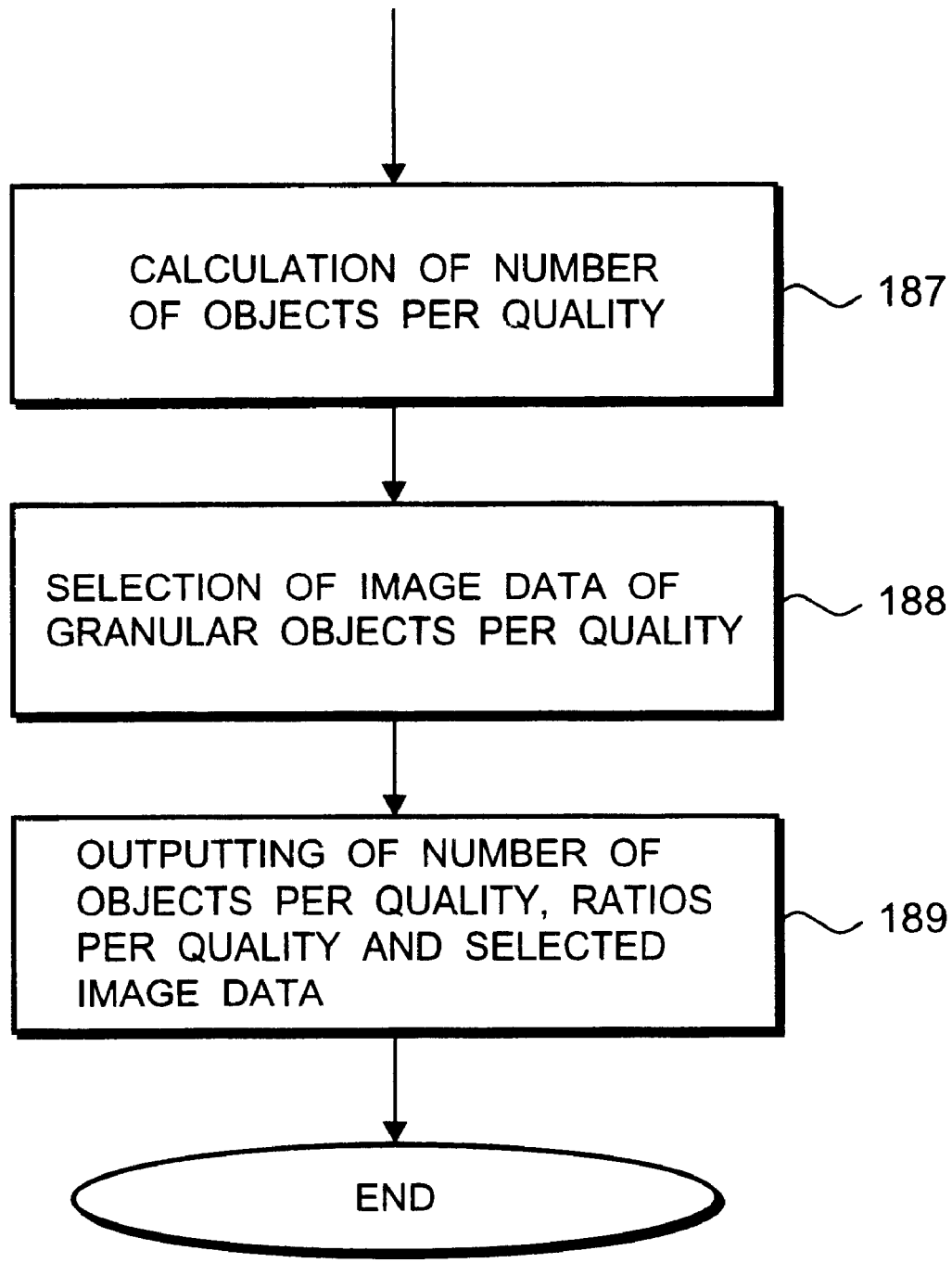
FIG. 19 is a flow chart showing another procedure for preparing the sample image.

When the images of 450 total objects are outputted as granular objects, the above explanation applies. However, in case, due to the size of the sheet to be printed by the color printer 5 or the resolution by the display 6, only 100 granular objects or so as granular objects can be printed or displayed, the output is processed as shown in FIG. 19. That is, instead of the step 167 in FIG. 17, the number of granular objects on a quality to quality basis is calculated from the ratio of the number of granular objects and the 100 granular objects (step 187) for which the printing or the displaying is possible. According to the number of granular objects for each quality, the related image data is arbitrarily selected from the data in the memory section 3c (step 188). The number and the ratio of granular objects obtained and the image data selected for the 100 granular objects are set to a predetermined format and outputted from the output port 4c to the color printer 5 or the color display 6 (step 189). Thus, the quality evaluation data for the grains as shown in FIG. 20 as one printing example is completed.

Figure 21:
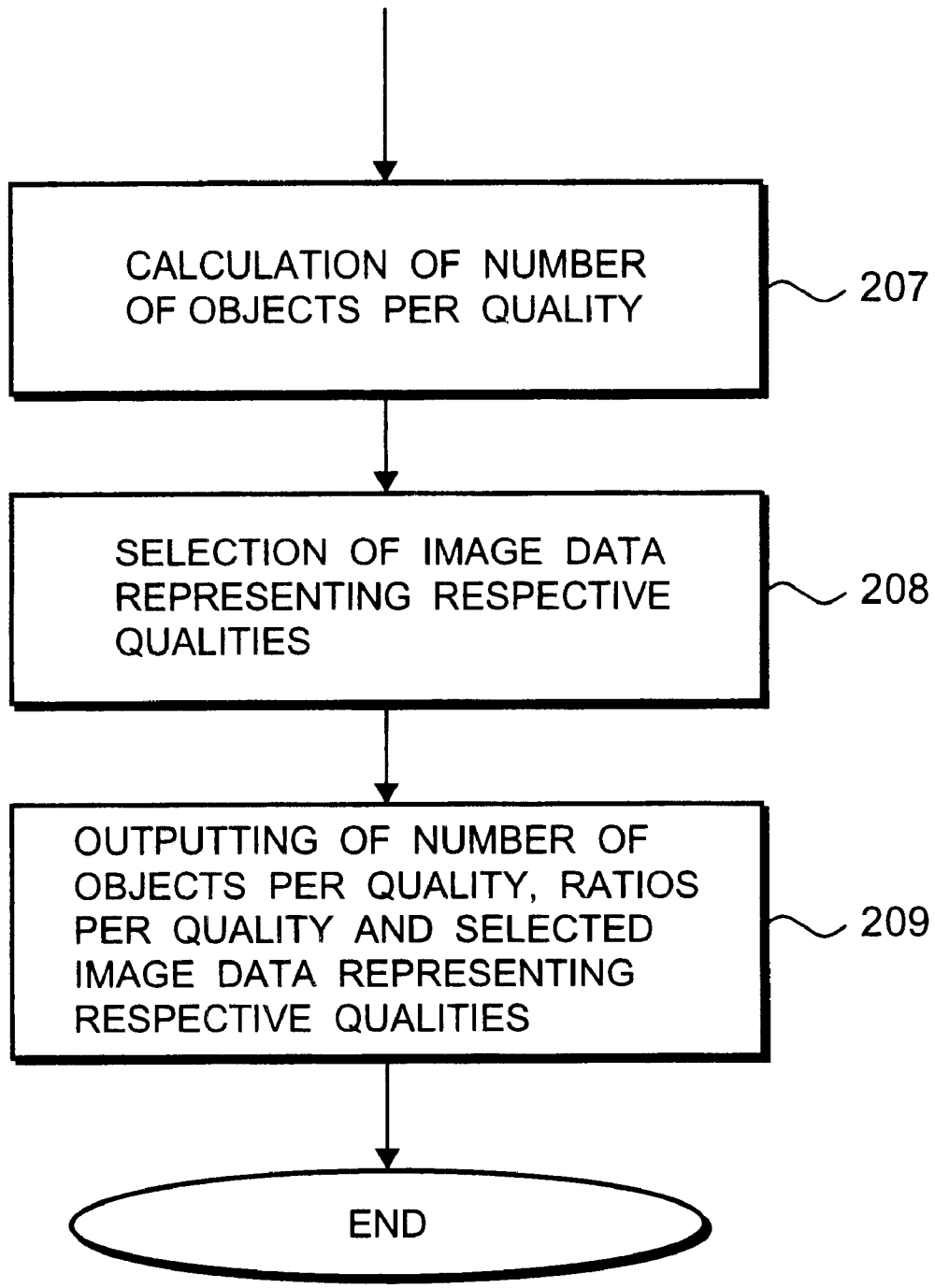
FIG. 21 is a flow chart showing another procedure for preparing the sample image.

In the embodiment shown in FIG. 21 which is separate from the embodiment shown in FIG. 19, in stead of the step 167 in FIG. 17, the number of granular objects for each quality is calculated from the ratio of granular objects for each quality and the 100 granular objects for which the printing or displaying is possible (step 207). And, from the image data stored in the memory section 3c, the image data representing the quality is selected, one at a time, for each quality (step 208). Next, the image data copied and processed from image data representing the number, the ratio and the quality of granular objects for each quality are set to a predetermined format and outputted from the output port 4c to the color printer 5 or the color display 6 (step 209).

The above explained embodiment is one in which only one light source (surface light source) is used to irradiate the granular objects on the rotary disk in a slanted angle, and the slanted transmission light in only one direction from the objects is received by the light receiving element. However, as already explained, in order to precisely detect the cracks in the granular objects, only one light source irradiating the objects in a slanted angle and the detection of the transmitted light coming from only one direction based on the one light source are not sufficient. The second embodiment of the invention is aimed at providing an apparatus for evaluating quality of a granular object in which the capability of detection of cracks in the granular objects is highly enhanced.

Figure 22:
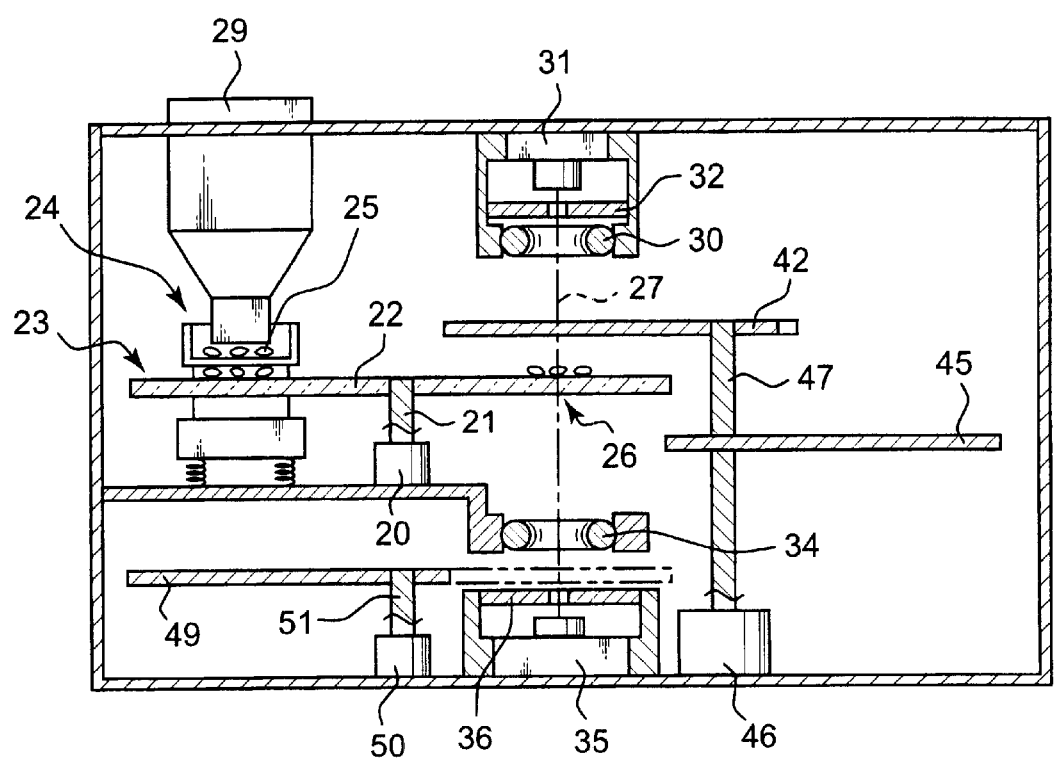
FIG. 22 is a diagrammatic side sectional view showing an internal arrangement of a measuring section of a second embodiment according to the invention.
Figure 23:
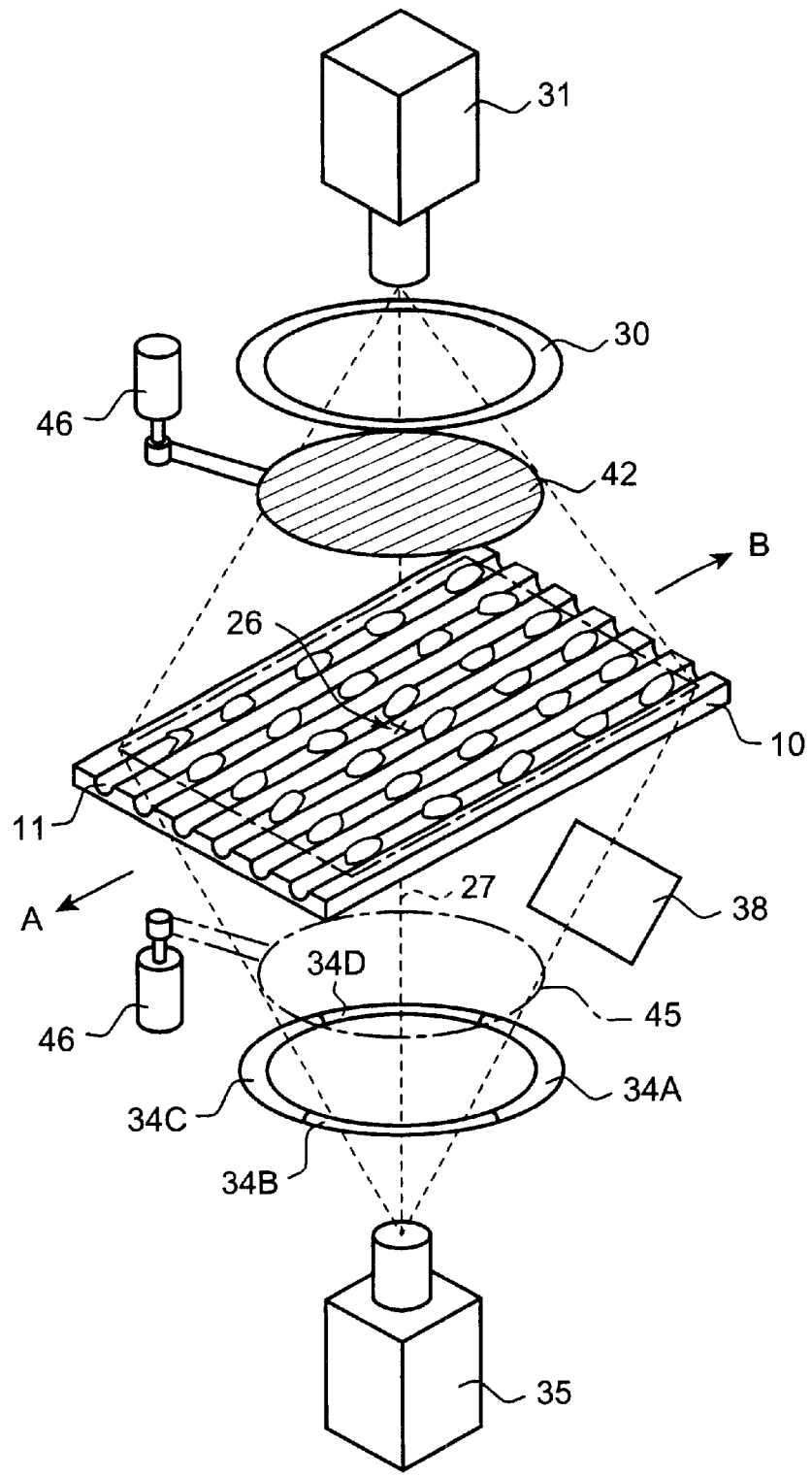
FIG. 23 is a diagrammatic perspective view showing the granular object holding means.

The second embodiment of the apparatus according to the invention are now explained with reference to FIGS. 22–26. In this second embodiment, the surface light source 38 for irradiating the objects in a slanted angle and the lower light source 34 (see FIGS. 1 and 4) are not used, but four separate arcuate light sources 34A, 34B, 34C and 34D which, in combination, constitute a circular or ring-like light source similar to the lower light source 34 of the first embodiment are used as a lower light source as shown in FIGS. 22 and 23. The four light sources 34A to 34D are supplied with electric power independently from each other. Thus, the light sources 34A–34D are turned ON simultaneously or sequentially turned ON one by one. If the light sources are turned ON one by one, the light is irradiated on the granular objects from the four directions, namely, from above, below, right and left, as explained later with reference to FIG. 25.

Figure 24:
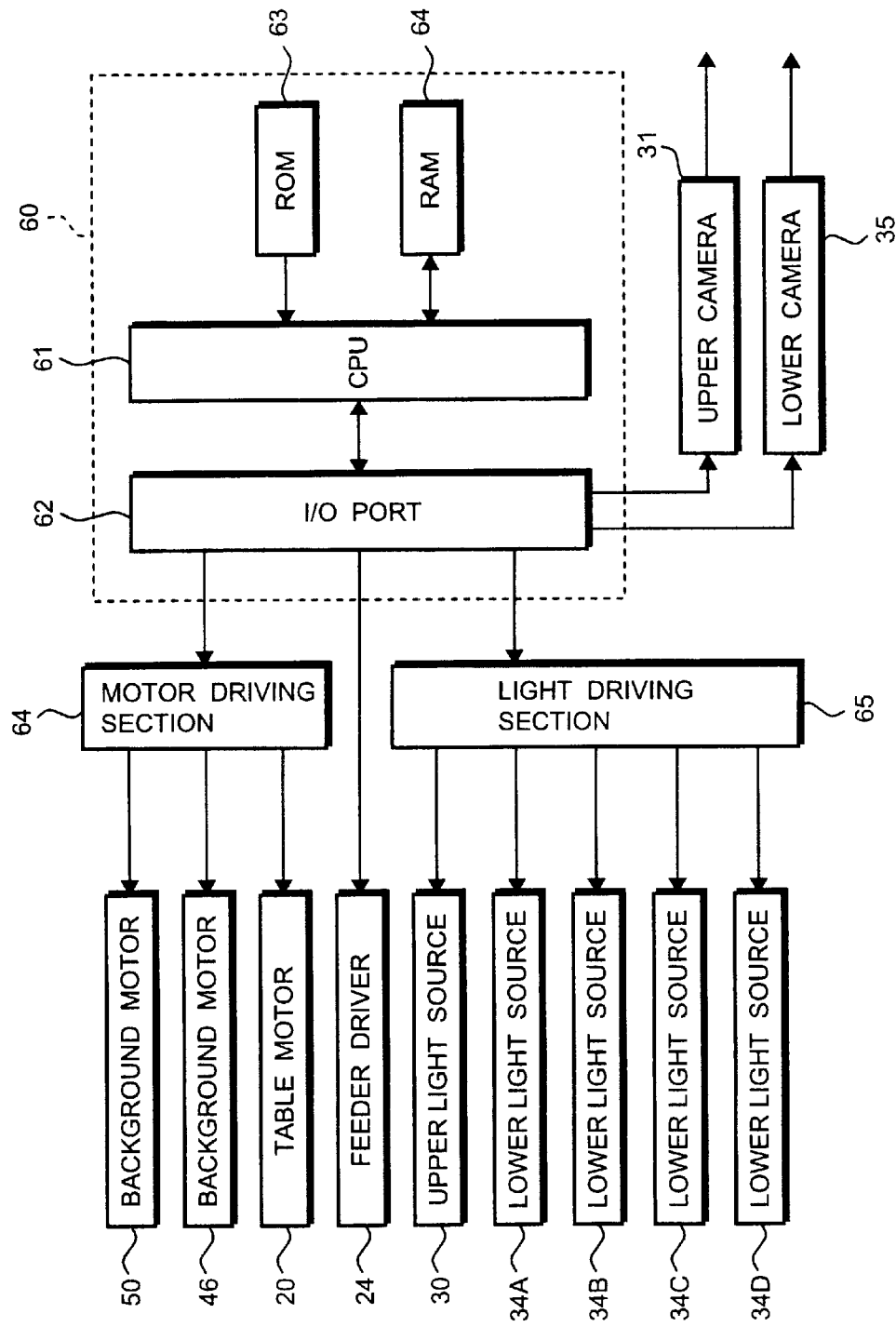
FIG. 24 is a control block diagram of the image taking means of a second embodiment.

FIG. 24 is a block diagram showing a control means 60 of the image taking means 2 in this second embodiment. The difference from the first embodiment is only that the light source driving section 65 drives the light sources 34A–34D independently from each other.

As other remaining construction of this second embodiment is substantially the same as that of the first embodiment, no explanation is made here.

In the second embodiment, various measurements of the transmission and reflection light are effected as follows.

The measuring of the upper transmission light is conducted by rotating the background plate motor 46 a predetermined amount and the milky white plate 43 is moved to the position of the viewing point 27, turning ON all the lower light sources 34A, 34B, 34C, 34D and taking an image (step 705 in FIG. 8) of the transmission light of the granular objects by the upper camera 31 from above. Then, the image data is sent to the image data processing means 3.

The measuring of the upper reflection light is conducted by rotating the background plate motor 46 a predetermined amount and the black plate 44 is moved to the position of the viewing point 27, turning OFF all the light sources 34A, 34B, 34C, 34D and then turning ON the upper light source 30, and taking an image (step 706 in FIG. 8) of the reflection light of the granular objects by the upper camera 31 from above. Then, the image data is sent to the image processing means 3.

Similarly the measuring of the lower transmission light is conducted by rotating the background plate motor 46 a predetermined amount and the milky white plate 40 is moved to the position of the viewing point 27, turning ON the upper light source 30, and taking an image (step 707 in FIG. 8) of the transmission light of the granular objects by the lower camera 35 from below. Then, the image data is sent to the image processing means 3.

Also, similarly, the measuring of the lower reflection light is conducted by rotating the background plate motor 46 a predetermined amount and the black plate 41 is moved to the position of the viewing point 27, turning OFF the upper light source 30 and turning ON all the lower light sources 34A, 34B, 34C, 34D and taking an image (step 708 in FIG. 8) of the reflection light of the granular objects by the lower camera 31 from below. Then, the image data is sent to the image processing means 3.

Finally, the measuring of the slanted transmission light is conduct ed by rotating the background plate motor 46 a predetermined amount and no background plate 48 is moved to the position of the viewing point 27, rotating the background motor 50 a predetermined amount and moving the black plate 49 to the position of the viewing point, switching ON any one of the light sources 34A, 34B, 34C, 34D at one time by using, for example, a multiplexer, and taking an image (step 709 in FIG. 8) of the slanted transmission light of the granular objects by the upper camera 31 from above. Then, the image data is sent to the image processing means 3.

Figure 26:
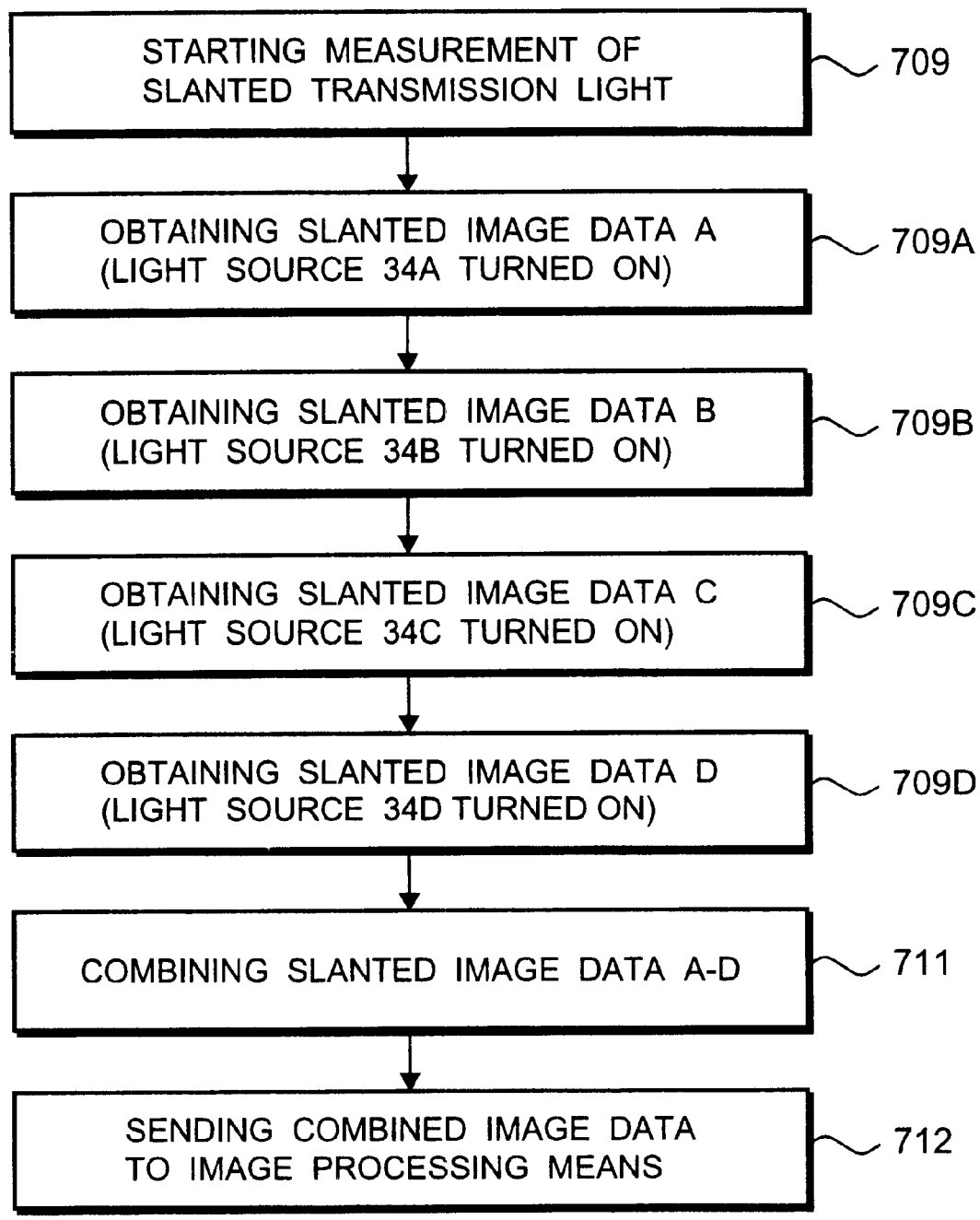

The measuring of the slanted transmission light in this second embodiment is explained with reference to FIG. 25(A)–25(D) and FIG. 26. FIG. 26 is a flow chart of detecting a crack.

FIG. 25(A) shows that, with respect to the slanted transmission light when the light source 34A is turned ON, the light is not perpendicularly directed to the one crosswise crack surface on the rice grain located near the light source and, as a result, the crack appears faintly. Also, on the rice grain located far from the light source, since the amount of the light is not sufficient and one side becomes a shade, nothing can be recognized clearly. Further, as to the grain having a lengthwise crack, the crack can be recognized clearly since the light is perpendicularly directed to the crack surface.

As shown in FIG. 25(B), with respect to the slanted transmission light when the light source 34B is turned ON, the light is perpendicularly directed to the one crosswise crack surface on the rice grain located near the light source and, as a result, the crack can be recognized clearly. On the rice grain located far from the light source, since the amount of the light is not sufficient and one side becomes a shade, nothing can be recognized clearly. Further, as to the grain having a lengthwise crack, the crack can be recognized faintly since the light is not perpendicularly directed to the crack surface.

As shown in FIG. 25(C), with respect to the slanted transmission light when the light source 34C is turned ON, the opposite side of the light source 34A becomes a shade, so that the crack can be recognized clearly concerning the lengthwise crack.

As shown in FIG. 25(D), with respect to the slanted transmission light when the light source 34D is turned ON, the opposite side of the light source 34B becomes a shade, so that crack can be recognized clearly concerning the rice grain located near the light source. Thus, when the images from the light source 34A to the light source 34D are combined, the crack can be detected highly precisely.

According to the flow chart of FIG. 26, when the measuring of the slanted transmission light is started (step 709 in FIG. 8), the image data as the images obtained on turning ON the light source 34A are stored (step 709A). Next, the light source 34A is turned OFF, and the image data as the images obtained on turning ON the light source 34B are stored (step 709B). Similarly, the images obtained when the light source 34B is turned OFF and the light source 34C is turned ON, and the images obtained when the light source 34C is turned OFF and the light source 34D is turned ON are stored respectively as the image data (step 709C, step 709D). And, the images of four kinds obtained by the step 709A to the step 709D are combined on the screen (step 711), and this results in the images of one rice grain irradiated from the four directions by the light sources. In this way, there is no influence caused by the shade due to the distance from the light source or by the lack of the amount of light, unlike in the one direction light source. Also, even when the crack is in a lengthwise direction, the crack detection is enhanced because the irradiation is from the four directions. The image data are sent to the image processing means 3.

As the other operation of this second embodiment is substantially the same as that of the first embodiment, the explanation thereof is not repeated here.

The granular object quality evaluation apparatus explained above is one which enables the evaluation of cracks and qualities of the grains and, when the crack detection is performed, the minimum elements required in the measuring section are three elements, namely, the granular object holding means, the light sources which can irradiate from a plurality of directions, and the image taking means, and when the quality detection is performed, the minimum elements required in the measuring section are four elements, the granular object holding means, the light sources which can irradiate from a plurality of directions, the background plate serving as reference of at least the transmission light of the granular object, and the image taking means. In the foregoing examples, as the background plate means, a plurality of plates such as a reflection light background plate and a transmission light background plate have been used. However, the background plates, with the exception of the transmission light background plate, are not essential and they may or may not be used.

As has been explained hereinabove, according to the invention, the granular object supplied by the granular object holding means is irradiated on both the front side and the back side of the granular object by the light from the light source, so that, by the image taking means, a plurality of image signals can be obtained from the reflection image signal of both the front and back sides and the transmission image signal of both the front and back sides, and the image signals of the granular object can be taken from different viewing points of the image taking means. Thus, by comparing the reflection images of the front side and the back side, or by comparing the transmission images of the front side and the back side of the granular object, it is possible to extract the feature items of the granular object. For example, even when a slight black spot exists only on one side of the granular object, no erroneous measurement occurs, and the quality evaluation of the granular object can be carried out accurately, thus enabling to enhance the precision in the results of the analysis. Also, since the quality evaluation is made based on the image signal obtained from the granular object, the sample image is prepared from such image signal, and the evaluation results and the sample image are simultaneously printed or displayed, the reliability of the results of the quality evaluation has been highly enhanced.

In the embodiment in which a plurality of arcuate light sources which, in combination, form a ring-like light source are sequentially turned on by the light source driving means, since the light to four directions, that is, two ends of the rice grain in lengthwise directions and two ends of the rice grain in the widthwise directions can be respectively irradiated, it is possible to prevent the shade that may be caused by the lack of the amount of light when the light source is far away, the shade that may be caused by the overlapping of the rice grains, or the shade by the granular object holding means. Thus, there is no possibility of overlooking a crack on one side or a lengthwise crack in the rice grain. In this way, the slanted light images can be obtained from many directions so that, by extracting the feature items of the cracked grain, the crack evaluation can be performed with a high precision.

The image taking means is equipped with an upper camera disposed above the granular object holding means and adapted to take the reflection image from the front side of the granular object, the transmission image from the front side of the granular object, and the slanted transmission image, and a lower camera disposed below the granular object holding means and adapted to take the reflection image from the back side of the granular object and the transmission image from the back side of the granular object so that, by at least two cameras, it is possible to obtain five kinds of image signals, namely, the reflection image from the front side, the transmission image from the front side, the reflection image from the back side, and the transmission image from the back side, and the slanted transmission image, of the granular object, and it is enabled, by the simple construction, to perform the quality evaluation with precision. In the case where a plurality of light sources are arranged below the granular object holding means, a plurality of slanted transmission images are obtained.

The light source is equipped with an upper light source provided above the granular object holding means and adapted to irradiate the front side of the granular object, a lower light source provided below the granular object holding means and adapted to irradiate the back side of the granular object, and a surface light source provided at a side of the lower light source and adapted to irradiate the granular object in a slanted angle. Thus, when the upper light source, the lower light source and the surface light source are selectively switched ON or OFF, it is possible to obtain the reflection light from the front side, the transmission light from the front side, the reflection light from the back side, the transmission light from the back side, and the slanted transmission light from one side of the granular object, and it is enabled to obtain image signals by the cameras.

If the lower light source is formed by a plurality of arcuate light sources which are selectively switched ON or OFF, the above surface light source can be dispensed with.

Where each of the upper light source and the lower light source is formed in a circular light source, and the measuring point is located at the center of the circular light source, the light irradiates the measuring point from all angles (360°) so that it is possible to prevent the shades otherwise caused by the overlapping of granular objects or by the presence of the granular object holding means, and to obtain clear and distinct image signals.

The background plate means comprises a plurality of background plates including a lower reflection background plate, a lower transmission light background plate and a slanted transmission light background plate provided below the granular object holding means, and an upper reflection light background plate and an upper transmission light background plate provided above the granular object holding means. Thus, when the lower reflection image, the lower transmission image, the slanted transmission image(s), the upper reflection image and the upper transmission image are obtained one by one, it is possible to select a background plate most suitable to a given image.

The arithmetic and control means is provided with a control means for controlling the image taking means, the light sources and the background plates. The control means acts, when the upper camera takes the transmission images of the front side of the granular object, to turn on the lower light source(s) and to select the lower transmission light background plate, when the upper camera takes the reflection images of the front side of the granular object, to turn on the upper light source and to select the lower reflection light background plate, when the lower camera takes the transmission image signal of the back side of the granular object, to turn on the upper light source and to select the upper transmission light background plate, when the lower camera takes the reflection image signal of the back side of the granular object, to turn on the lower light source(s) and to select the upper reflection light background plate, when the upper camera takes the slanted light transmission image signal of one side of the granular object, to turn on the slanted light source and to select the slanted light transmission background plate. In the case where a plurality of arcuate light sources are used as the lower light source, when the upper camera takes the slanted light transmission image signal from a plurality of directions, the plurality of light sources are sequentially turned on and the slanted light transmission background plate is selected. Thus, when the programs for performing the repeated operation for the image-takings are stored in the control means, the obtaining of the images can be automated.

The granular object holding means in the form of a rotary disk, transfers continuously the granular objects supplied from one end of the rotary disk to a measuring point, the granular objects at the measuring point being obtained as a plurality of image signals by the image taking means and, subsequently, the granular objects on the rotary disk being discharged continuously from the other end thereof. Thus, when the quality measurement of the granular objects is performed a number of times, new granular objects may be continuously transferred to the measuring point only by rotating the rotary disk, and the granular objects having been measured may be continuously discharged so that the operation of the measurement becomes simple.

On the other hand, when the granular object holding means is formed such that the granular objects are lined-up on a slide plate in a plurality of rows with the granular objects being in a single layer state, it is enabled, when a plurality of image signals are obtained by the image taking means, to obtain the image signals of the granular objects in a state in which the image signals of the granular objects are orderly lined-up on the slide plate. Thus, as compared with disorderly image signals of the granular objects, the well-ordered image signals have better appeal to the eyes.

The arithmetic and control means obtains optical information and shape information from the granular object whose quality and/or crack is known, stores a granular object quality evaluation formula obtained by the analysis in which the quality of the granular object whose quality and/or crack is known is used as objective variables and the optical information and the shape information are used as explanatory variables, and carries out the quality evaluation process by the granular object quality evaluation formula. Thus, if the value to be applied to the quality evaluation formula is obtained faster, the quality evaluation can be made faster accordingly.

The arithmetic and control means prepares a sample image of each granular object on a quality to quality basis based on the optical information obtained by the image processing section, calculates the number of granular objects on the quality to quality basis based on the ratio of the number of the granular objects and the predetermined total number of the granular objects, the sample images being arranged according to the results of the calculation, and the results of the granular object quality evaluation and the sample images being simultaneously displayed or printed. Thus, even when the number of the granular objects which have been subjected to the taking of the images is larger than the total number that is predetermined for the sample images, the images for the quality evaluation are taken out from the images of the granular objects, and the sample images are prepared according to the number of granular objects on the quality to quality basis calculated based on the total number of granular objects and the granular objects ratio. The sample images correspond to the quality evaluation granular object number ratio. Thus, even when the total number of granular objects is different from the number of the granular objects subjected to the image taking, the sample images remain highly reliable.

The optical information include hue, saturation, and intensity of the grain object, and the shape information include data such as length, width and size or area of the granular object provided by the intensity of the granular object within the optical information. The difference in the degrees of intensity obtained from the transmission light of the granular object can be detected as representing an outward shape, a colored portion of the granular object, or an inward shape in accordance with endoplasm, as the data including various factors. From the data based on the reflection light from the granular objects, the colors of the granular objects can be clearly and definitely grasped. Thus, from the optical information by the transmission and the reflection, it has become possible to make evaluation concerning the outward shapes, endoplasm, and colors.

While the invention has been described in its preferred embodiments, it is to be understood that the words which have been used are words of description rather than limitation and that changes within the purview of the appended claims may be made without departing from the true scope of the invention as defined by the claims.

What is claimed is:

1. A method for evaluating the quality of granular objects, said method comprising the steps of:
   irradiating said granular objects selectively from a front side and a back side of said granular objects;
   taking a reflection light image and a transmission light image from the front and back sides of each of said irradiated granular objects;
   obtaining optical information of each of said granular objects by image-processing said reflection light image and said transmission light image;
   obtaining shape information of said granular objects based on said optical information;

determining the quality of each of said granular objects based on said optical information and said shape information, said quality of granular objects including such quality as complete and incomplete granular objects;

counting the numbers of the granular objects per quality and obtaining ratios per quality of the granular objects against the total number of the granular objects;

preparing sample images of said granular objects per quality by processing said optical information; and simultaneously displaying or printing the respective numbers of the granular objects per quality, said ratios per quality of the granular objects and said sample images of the granular objects.

2. A method of evaluating the quality of granular objects according to claim 1, in which said sample images per quality are displayed or printed after having been arranged in a predetermined format according to the respective numbers of the granular objects per quality calculated based on said ratios and the total number of the granular objects.

3. A method of evaluating the quality of granular objects according to claim 1 or 2, further comprising a step of establishing a granular object quality evaluation formula based on analysis in which the quality of the granular object whose quality is known is used as objective variables and the optical information and the shape information obtained from the granular object whose quality is known are used as explanatory variables, wherein a quality for the granular objects whose quality is unknown is evaluated based on said granular object quality evaluation formula and the optical information and the shape information obtained therefrom.

4. A method for evaluating the quality of granular objects according to claim 1 or 2, in which said optical information includes hue, saturation and intensity of the granular objects.

5. A method for evaluating the quality of granular objects according to claim 4, in which said shape information including length, width and size or area of the granular objects is obtained from said intensity within said optical information.

6. An apparatus for evaluating the quality of granular objects, said apparatus comprising:

granular object holding means formed of a material which transmits light incident thereon;

light source means for irradiating light on front and back sides of each of said granular objects held by said granular object holding means;

background means for establishing references to reflection light or transmission light from or through each of said granular objects;

image taking means for obtaining image signals of reflection light images and transmission light images from both the front and back sides of each of said granular objects, and slanted light images of one of said front and back sides of each of said granular objects;

image processing means for converting said plurality of image signals obtained by said image taking means into optical information relating to the quality of the granular objects, and converting said optical information into shape information;

arithmetic and control means for determining the quality of the granular objects per quality based on said optical information and said shape information which are obtained by said image processing means; and indicating means for displaying or printing simultaneously the results of quality evaluation obtained by said arithmetic and control means and said shape information obtained by said image processing means.

7. An apparatus for evaluating the quality of granular objects according to claim 6, in which one of said light source means comprises four separate light sources which irradiate said granular objects diagonally from four directions, said four light sources being turned on or off simultaneously or independently from each other, a plurality of said slanted light images being obtained when said four light sources are sequentially turned on.

8. An apparatus for evaluating the quality of granular objects according to claim 6 or 7, in which said arithmetic and control means stores sample images of said granular objects per quality and calculates the numbers of the granular objects per quality based on the ratios of the granular objects per quality and the total number of the granular objects, arranges the order of the stored sample images according to the results of the above calculation, and outputs the results of the quality evaluation of the granular objects and said arranged sample images to said indicating means.

9. An apparatus for evaluating the quality of granular objects according to claim 6 or 7, in which said arithmetic and control means stores a granular object evaluation formula obtained by analysis in which the quality of the granular object whose quality is known is used as objective variables and the optical information and the shape information obtained from the granular object whose quality is known are used as explanatory variables, wherein a quality of the granular object whose quality is unknown is obtained by applying the optical information and the shape information obtained from said image processing means to said granular object quality evaluation formula.

10. An apparatus for evaluating the quality of granular objects according to claim 6 or 7, in which said light source means is of a circular or a ring-like shape.

11. An apparatus for evaluating the quality of granular objects according to claim 6 or 7, in which said optical information includes hue, saturation and intensity of the granular objects.

12. An apparatus for evaluating the quality of granular objects according to claim 11, in which said shape information including length, width and size or area of the granular objects is obtained based on intensity within said optical information.

* * * * *

UNITED STATES PATENT AND TRADEMARK OFFICE
CERTIFICATE OF CORRECTION

PATENT NO.    : 6,427,128 B1  Page 1 of 1
DATED         : July 30, 2002
INVENTOR(S)   : Satoru Takashita et al.

It is certified that error appears in the above-identified patent and that said Letters Patent is hereby corrected as shown below:

Column 3,
Line 21, delete "go".

Column 5,
Line 30, replace "he" with -- the --.

Column 6,
Line 9, replace "ROW" with -- ROM --.

Column 11,
Line 58, replace "$F_{0\text{-}f9}$" with -- $F_0$-$F_9$ --.

Column 14,
Line 26, replace "conduct ed" with -- conducted --.

Signed and Sealed this

Eighth Day of April, 2003

JAMES E. ROGAN
*Director of the United States Patent and Trademark Office*